United States Patent
Lee et al.

(10) Patent No.: US 10,640,797 B2
(45) Date of Patent: *May 5, 2020

(54) MICROORGANISMS FOR PRODUCING DIAMINE AND PROCESS FOR PRODUCING DIAMINE USING THEM

(71) Applicant: CJ CHEILJEDANG CORPORATION, Seoul (KR)

(72) Inventors: Kyoung Min Lee, Seoul (KR); Su Jin Park, Seoul (KR); Hee Kyoung Jung, Seoul (KR); Young Lyeol Yang, Gyeonggi-do (KR); Hong Xian Li, Seoul (KR); Hye Won Um, Gyeonggi-do (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 15/306,758

(22) PCT Filed: Mar. 27, 2015

(86) PCT No.: PCT/KR2015/003066
§ 371 (c)(1),
(2) Date: Oct. 25, 2016

(87) PCT Pub. No.: WO2015/163592
PCT Pub. Date: Oct. 29, 2015

(65) Prior Publication Data
US 2017/0159085 A1 Jun. 8, 2017

(30) Foreign Application Priority Data
Apr. 25, 2014 (KR) .................. 10-2014-0049871

(51) Int. Cl.
*C12N 1/20* (2006.01)
*C12P 13/00* (2006.01)

(52) U.S. Cl.
CPC .............. *C12P 13/001* (2013.01); *C12N 1/20* (2013.01); *C12P 13/00* (2013.01); *C12Y 203/01057* (2013.01)

(58) Field of Classification Search
None
See application file for complete search history.

(56) References Cited

U.S. PATENT DOCUMENTS

| | | | | |
|---|---|---|---|---|
| 8,481,293 | B2* | 7/2013 | Lee | C12P 13/001 435/128 |
| 2010/0203599 | A1* | 8/2010 | Lee | C12P 13/001 435/128 |
| 2014/0134682 | A1* | 5/2014 | Wittmann | C12N 9/88 435/129 |
| 2018/0273992 | A1* | 9/2018 | Lee | C12Y 203/01057 |

FOREIGN PATENT DOCUMENTS

| | | |
|---|---|---|
| CN | 101389765 A | 3/2009 |
| CN | 101679964 A | 3/2010 |
| CN | 103492553 A | 1/2014 |
| JP | 2009-531042 A | 9/2009 |
| JP | 2014-507152 A | 3/2014 |
| JP | 2016-514466 A | 5/2016 |
| KR | 10-0159812 B | 8/1998 |
| KR | 10-0620092 B | 8/2006 |
| KR | 1020120064046 A | 6/2012 |
| KR | 1020130082478 A | 7/2013 |
| KR | 2014-0012099 A | 1/2014 |
| TW | 201546277 A | 12/2015 |
| WO | 2006/005603 A1 | 1/2006 |
| WO | 2006/065095 A1 | 6/2006 |
| WO | 2009/096689 A2 | 8/2009 |
| WO | 2009/125924 A2 | 10/2009 |
| WO | 2009/125992 A2 | 10/2009 |
| WO | 2012-114256 A1 | 8/2012 |
| WO | 2013-093737 A1 | 6/2013 |
| WO | 2013/105827 A2 | 7/2013 |
| WO | 2013105827 A2 | 7/2013 |
| WO | 2014-148743 A1 | 9/2014 |

OTHER PUBLICATIONS

UniProt Accession No. J0JMF3_ALCFA, published Oct. 3, 2012 (Year: 2012).*
UniProt Accession No. J7SZM4_STEMA, published Oct. 31, 2012 (Year: 2012).*
NCBI Reference Sequence: WP_014647312.1, "MFS transporter [Stenotrophomonas maltophilia]," first publication date: Jul. 19, 2013, two pages.
UniProtKB: J0JMF3 (J0JMF3_ALCFA), Gene: QWA_00075, Organism: *Alcaligenes faecalis* subsp. *faecalis* NCIB 3687, publication date: Oct. 3, 2012, three pages.
Genbank, "Major facilitator transporter [*Alcaligenes faecalis* subsp. *faecalis* NCIB 8687]," Accession No. EJC65209, Jun. 18, 2012, two pages.
Kind et al., "Identification and Elimination of the Competing N-Acetyldiaminopentane Pathway for Improved Production of Diaminopentane by Corynebacterium glutamicum," Applied and Environmental Microbiology 76(15): 5175-5180, Aug. 2010.
NCBI, "Membrane protein [Stenotrophomonas maltophilia]," Accession No. WP_01467312, May 28, 2013, one page.

(Continued)

*Primary Examiner* — Richard C Ekstrom

(74) *Attorney, Agent, or Firm* — Cooley LLP

(57) ABSTRACT

The present invention relates to a microorganism for producing diamine, in which activity of a protein having an amino acid sequence of SEQ ID NO: 6 or an amine acid sequence having 42% or higher sequence homology with SEQ ID NO: 6 is introduced or enhanced, and a method of producing diamine using the same.

5 Claims, No Drawings
Specification includes a Sequence Listing.

(56) References Cited

OTHER PUBLICATIONS

UNIPROTKB—G0F1K2 (G0F1K2_ECOLX), Protein: Spermidine N(1)-acetyltransferase (Diamineacetyltransferase) (SAT), Gene: UMNF18_2013, Organism: *Escherichia coli* UMNF18, last modified: Oct. 19, 2011, four pages.

Genbank: ADH92029.1, "Major facilitator superfamily MFS_1 [Arcanobacterium haemolyticum DSM 20595]," accessed Jan. 28, 2014.

Kind et al., "Metabolic engineering of cellular transport for overproduction of the platform chemical 1,5-diaminopentane in Corynebacterium glutamicum," Metabolic Engineering 13: 617-627, 2011.

Qian et al., "Metabolic Engineering of *Escherichia coli* for the Production of Putrescine: A Four Carbon Diamine," Biotechnology and Bioengineering 104: 651-662, 2009.

Schneider et al., "Improving putrescine production by Corynebacterium glutamicum by fine-tuning ornithine transcarbamoylase activity using a plasmid addiction system," Appl. Microbiol. Biotechnol. 95: 169-178, 2012.

Schneider and Wendisch, "Putrescine production by engineered Corynebacterium glutamicum," Appl. Microbiol. Biotechnol. 88: 859-868, 2010.

Soksawatmaekhin et al., "Excretion and uptake of cadaverine by CadB and its physiological functions in *Escherichia coli*," Molecular Microbiology 51(5): 1401-1412, 2004.

Tabor and Tabor, "Polyamines in Microorganisms," Microbiological Reviews 49(1): 81-99, Mar. 1985.

Tomitori et al., "Multiple polyamine transport systems on the vacuolar membrane in yeast," Biochem. J. 353: 681-688, 2001.

Schneider et al., "Biotechnological production of polyamines by Bacteria: recent achievements and further perspectives," Appl Microbiol Biotechnol (2011) 91:17-30.

Qian et al., "Metabolic Engineering of *Escherichia coli* for the Production of Cadaverine: A Five Carbon Diamine," Biotechnology and BioEngineering 108(1): 93-103, Jan. 1, 2011.

Database UniProtKB, [online], Accession No. J0JMF3, <http://www.uniprot.org/uniprot/J0JMF3.fasta?version=8>, Feb. 19, 2014 uploaded, [retrieved on Jul. 24, 2017], one page.

Database UniProtKB, [online], Accession No. J7SZM4, <http://www.uniprot.org/uniprot/J7SZM4.fasta?version=9, Feb. 19, 2014 uploaded, [retrieved on Jul. 24, 2017], one page.

Igarashi, K., et al., "Characteristics of Cellular Polyamine Transport n Prokaryotes and Eukaryotes," Plant Physiology and Biochemistry. 48(7):506-512 (2010).

* cited by examiner

MICROORGANISMS FOR PRODUCING DIAMINE AND PROCESS FOR PRODUCING DIAMINE USING THEM

CROSS-REFERENCES TO RELATED APPLICATIONS

This application is a U.S. national phase application of International PCT Patent Application No. PCT/KR2015/003066, which was filed on Mar. 27, 2015, which claims priority to Korean Patent Application Nos. 10-2014-0049871, filed Apr. 25, 2014. These applications are incorporated herein by reference in their entireties.

STATEMENT REGARDING SEQUENCE LISTING

The Sequence Listing associated with this application is provided in text format in lieu of a paper copy, and is hereby incorporated by reference into the specification. The name of the text file containing the Sequence Listing is HANO_051_00US_ST25.txt. The text file is 70 KB, was created on Oct. 25, 2016, and is being submitted electronically via EFS-Web.

TECHNICAL FIELD

The present disclosure relates to a microorganism for producing diamine and a method of producing diamine using the same.

BACKGROUND ART

Biogenic amines (BAs) are nitrogenous compounds which are mainly produced by decarboxylation of amino acids or by rumination and transamination of aldehydes and ketones. These biogenic amines are low molecular weight compounds and synthesized in the metabolism of microorganisms, plants and animals, and thus biogenic amines are known as components frequently found in these cells. In particular, biogenic amines are polyamines such as spermidine, spermine, putrescine or 1,4-butanediamine, and cadaverine.

In general, putrescine is an important raw material for production of polyamine nylon-4,6 which is produced by reacting putrescine with adipic acid. Putrescine is usually produced by chemical synthesis involving conversion of propylene to acrylonitrile and to succinonitrile.

As a production method of putrescine using a microorganism, a method of producing putrescine at a high concentration by transformation of *E. coli* and *Corynebacterium* has been reported (International Patent Publication No. WO06/005603; International Patent Publication No. WO09/125924; Qian Z D et al., Biotechnol. Bioeng. 104: 4, 651-662, 2009; Schneider et al., Appl. Microbiol. Biotechnol. 88: 4, 859-868, 2010; Schneider et al., Appl. Microbiol. Biotechnol. 95, 169-178, 2012). Furthermore, studies have been actively conducted on putrescine transporters in *E. coli*, yeast, plant and animal cells (K Igarashi, Plant Physiol. Biochem. 48: 506-512, 2010).

Meanwhile, cadaverine is a foul-smelling diamine compound produced by protein hydrolysis during putrefaction of animal tissues. Cadaverine has the chemical formula of $NH_2(CH_2)_5NH_2$, which is similar to that of putrescine.

Cadaverine serves as a component of polymers such as polyamide or polyurethane, chelating agents, or other additives. In particular, polyamide having an annual global market of 3.5 million tons is known to be prepared by polycondensation of cadaverine or succinic acid, and thus cadaverine has received much attention as an industrially useful compound.

Cadaverine is a diamine found in a few microorganisms (Tabor and Tabor, Microbrol Rev., 49:81-99, 1985). In the gram negative bacterium *E. coli*, cadaverine is biosynthesized from L-lysine by L-lysine decarboxylase. The level of cadaverine in *E. coli* is regulated by biosynthesis, degradation, uptake and export of cadaverine (Soksawatmaekhin et al., Mol Microbiol., 51:1401-1412, 2004).

DISCLOSURE

Technical Problem

The present inventors have made intensive efforts to investigate a protein having an ability to export diamine such as putrescine or cadaverine so as to improve diamine productivity in a microorganism having the diamine productivity. As a result, they found that a *Arcanobacterium haemolyticum*-derived protein or a protein having high amino acid sequence homology therewith has a diamine export activity, and this protein is introduced into a microorganism for producing diamine to enhance its activity, resulting in a remarkable increase in the ability to export diamine such as putrescine and cadaverine, thereby completing the present invention.

Technical Solution

An object of the present invention is to provide a microorganism for producing diamine.

Another object of the present invention is to provide a method of producing diamine, including the steps of (i) culturing the microorganism for producing diamine to obtain a cell culture; and (ii) recovering diamine from the cultured microorganism or the cell culture.

BEST MODE

In an aspect to achieve the above objects, the present invention provides a microorganism for producing diamine, in which activity of a protein having an amino acid sequence of SEQ ID NO: 6 or an amino acid sequence having 42% or higher sequence homology with SEQ ID NO:6 is introduced or enhanced.

As used herein, the term "diamine" collectively refers to a compound having two amine groups, and specific examples thereof may include putrescine and cadaverine. Putrescine is tetramethylenediamine which may be produced from ornithine as a precursor. Cadaverine is called 1,5-pentanediamine or pentamethylenediamine, which may be produced from lysine as a precursor. Such diamines are industrially applicable compounds that serve as valuable raw materials for synthesis of polymers such as polyamine nylon, polyamide or polyurethane.

As used herein, the term "protein having an amino acid, sequence of SEQ ID NO: 6" is a protein found in *Arcanobacterium haemolyticum*, and also called ARCH_0271. It was investigated that this protein retains high homology with a membrane protein of *Corynebacterium*, NCgl2522. In an embodiment of the present invention, ARCH_0271 protein is identified as a putative protein which is involved in diamine export in a strain having diamine productivity, thereby remarkably increasing diamine productivity.

Here, ARCH_0271 protein having the amino acid sequence of SEQ ID NO: 6 may be a protein that is encoded by a nucleotide sequence of SEQ ID NO: 5 or SEQ ID NO: 7. In the polynucleotide encoding the ARCH_0271 protein, however, various modifications may be made in the coding region provided that they do not change the amino acid sequence of the polypeptide expressed from the coding region, due to codon degeneracy or in consideration of the codons preferred by an organism in which the protein is to be expressed. Thus, the CE2495 protein may be encoded by various nucleotide sequences as well as by the nucleotide sequence of SEQ ID NO: 5 or SEQ ID NO: 7. Of them, the nucleotide sequence represented by SEQ ID NO. 7 is a sequence prepared by optimizing the ARCH_0271 gene (SEQ ID NO. 5) for codon usage of *Corynebacterium glutamicum*, but is not limited thereto.

Further, the ARCH_0271 protein of the present invention may be any protein having the amino acid sequence of SEQ ID NO: 6, or having 40% or higher, preferably 60% or higher, more preferably 80% or higher, much more preferably 90% or higher, even much more preferably 95% or higher, and most preferably 99% or higher homology therewith, as long as the protein exhibits a substantial diamine export activity. It is apparent that an amino acid sequence having such homology, of which a part is deleted, modified, substituted, or added, is also within the scope of the present invention, as long as the resulting amino acid sequence has a biological activity substantially equivalent or corresponding to the protein of SEQ ID NO: 6.

As used, herein, the term "protein having an amino acid sequence having 42% or higher sequence homology with the amino acid sequence of SEQ ID NO: 6" means any protein without limitation, as long as the protein has an amino acid sequence having 42% or higher sequence homology with the amino acid sequence of SEQ ID NO: 6 and it also has substantially diamine export activity. For example, the protein may be a protein having an amino acid sequence of SEQ ID NO: 23 or SEQ ID NO: 26, but is not limited thereto.

For example, the protein having the amino acid sequence of SEQ ID NO: 23 is a protein found in *Alcaligenes faecalis* subsp. *faecalis*, and also called QWA_00075. It was investigated that this protein retains 41% homology with a membrane protein of *Corynebacterium*, NCgl2522 and 42% homology with ARCH_0271 of *Arcanobacterium haemolyticum*. In an embodiment of the present invention, it was investigated that the QWA_00075 protein exhibits diamine export activity in a strain having diamine productivity, thereby remarkably increasing diamine productivity.

The QWA_00075 protein having the amino acid sequence of SEQ ID NO: 23 may be a protein that is encoded by a nucleotide sequence of SEQ ID NO: 22 or 24. In the polynucleotide encoding this protein, however, various modifications may be made in the coding region provided that they do not change the amino acid sequence of the polypeptide expressed from the coding region, due to codon degeneracy or in consideration of the codons preferred by an organism, in which the protein is to be expressed. Thus, this protein may be encoded by various nucleotide sequences as well as by the nucleotide sequence of SEQ ID NO: 22 or 24. Of them, the nucleotide sequence represented by SEQ ID NO: 24 is a sequence prepared by optimizing the QWA_00075 gene (SEQ ID NO: 22) for codon usage of *Corynebacterium glutamicum*, but is not limited thereto.

Further, the protein having the amino acid sequence of SEQ ID NO: 26 is a protein found in *Stenotrophomonas maltophilia*, and also called SMD_2351. It was investigated that this protein retains 52% homology with a membrane protein of *Corynebacterium*, NCgl2522 and 47% homology with ARCH_0271 of *Arcanobacterium haemolyticum*. In an embodiment of the present invention, it was investigated that the SMD_2351 protein exhibits diamine export activity in a strain having diamine productivity, thereby remarkably increasing diamine productivity.

The SMD_2351 protein having the amino acid sequence of SEQ ID NO: 26 may be a protein that is encoded by a nucleotide sequence of SEQ ID NO: 25 or 27. In the polynucleotide encoding this protein, however, various modifications may be made in the coding region provided that they do not change the amino acid sequence of the polypeptide expressed from the coding region, due to codon degeneracy or in consideration of the codons preferred by an organism in which the protein is to be expressed. Thus, this protein may be encoded by various nucleotide sequences as well as by the nucleotide sequence of SEQ ID NO: 25 or 27. Of them, the nucleotide sequence represented by SEQ ID NO: 27 is a sequence prepared by optimizing the SMD_2351 gene (SEQ ID NO: 25) for codon usage of *Corynebacterium glutamicum*, but is not limited thereto.

The term "homology", as used herein with regard to a sequence, refers to identity with a given amino acid sequence or nucleotide sequence, and the homology may be expressed as a percentage. In the present invention, a homology sequence having identical or similar activity to the given amino acid sequence or nucleotide sequence is expressed as "% homology". For example, homology may be identified using a standard software program which calculates parameters of score, identity and similarity, specifically BLAST 2.0, or by comparing sequences in a Southern hybridization experiment under stringent conditions as defined. Defining appropriate hybridization conditions are within the skill of the art (e.g., see Sambrook et al., 1989, infra), and determined by a method known to those skilled in the art.

As used herein, the term "microorganism for producing diamine" refers to a microorganism prepared by providing diamine productivity for a parent strain having no diamine productivity or a microorganism having endogenous diamine productivity. Specifically, the microorganism having diamine productivity may be a microorganism having putrescine or cadaverine productivity.

The "microorganism having putrescine productivity" may be, but is not limited to, a microorganism in which the activity of acetylglutamate synthase that converts glutamate to N-acetylglutamate, ornithine acetyltransferase (ArgJ) that converts acetyl ornithine to ornithine, acetylglutamate kinase (ArgB) that converts acetyl glutamate to N-acetylglutamyl phosphate, acetyl-gamma-glutamyl-phosphate reductase (ArgC) that converts acetyl glutamyl phosphate to N-acetyl glutamate semialdehyde, or acetylornithine aminotransferase (ArgD) that converts acetyl glutamate semialdehyde to N-acetylornithine is enhanced compared to its endogenous activity, in order to enhance the biosynthetic pathway from glutamate to ornithine, and the productivity of ornithine which is used as a precursor for putrescine biosynthesis is enhanced, but is not limited thereto.

Further, the microorganism having putrescine productivity may be a microorganism which is modified to have activity of ornithine carbamoyl transferase (ArgF) involved in synthesis of arginine from ornithine, a protein (NCgl1221) involved in glutamate export, and/or a protein (NCgl469) involved in putrescine acetylation weaker than its endogenous activity, and/or is modified to be introduced with activity of ornithine decarboxylase (ODC).

Here, as non-limiting examples, the acetyl gamma glutamyl phosphate reductase (ArgC) may have an amino acid sequence of SEQ ID NO: 15, the acetylglutamate synthase or ornithine acetyltransferase (ArgJ) may have an amino acid sequence of SEQ ID NO: 16, the acetyl glutamate kinase (ArgB) may have an amino acid sequence of SEQ ID NO: 17, and the acetylornithine aminotransferase (ArgD) may have an amino acid sequence of SEQ ID NO: 18. However, the amino acid sequences of respective enzyme proteins are not particularly limited thereto, and the enzymes may be proteins having amino acid sequences having 80% or higher, preferably 90% or higher, or more preferably 95% or higher homology therewith, as long as they have activities of the respective enzymes.

Further, as non-limiting examples, the ornithine carbamoyl transferase (ArgF) may have an amino acid sequence represented by SEQ ID NO: 19, the protein involved in glutamate export may have an amino acid sequence represented by SEQ ID NO: 20, and ornithine decarboxylase (ODC) may have an amino acid sequence represented by SEQ ID NO: 21. However, the amino acid sequences of respective enzyme proteins are not particularly limited thereto, and the enzymes may include amino acid sequences having 80% or higher, preferably 90% or higher, more preferably 95% or higher, or particularly preferably 97% or higher homology therewith, as long as they have activities of the respective enzymes.

Meanwhile, the "microorganism having cadaverine productivity" may be, but is not limited to, a microorganism prepared by additionally introducing or enhancing activity of lysine decarboxylase (LDC) in a microorganism having lysine productivity. For example, the microorganism may be one having enhanced lysine productivity in order to increase cadaverine production. A method of enhancing lysine productivity may be performed, by a known method which is predictable to those skilled in the art.

The lysine decarboxylase is an enzyme catalyzing conversion of lysine to cadaverine, and its activity is introduced or enhanced, thereby effectively producing cadaverine.

The lysine decarboxylase may have an amino acid sequence of SEQ ID NO: 33, but is not particularly limited thereto. The enzyme may have an amino acid sequence having 80% or higher, preferably 90% or higher, or more preferably 95% or higher homology therewith, as long as it has the above activity.

As used herein, the term "production" is a concept including extracellular release of diamine, for example, release of diamine into a culture medium, as well as production of diamine within a microorganism.

Meanwhile, the term "introduction of protein activity", as used herein, means that a microorganism having no endogenous protein is externally provided with an activity of the protein, and for example, it may be performed by introduction of a foreign gene. Further, the term "enhancement of protein activity" means that active state of the protein retained in or introduced into the microorganism is enhanced, compared to its intrinsic active state.

Non-limiting examples of the introduction or enhancement of the protein activity may include improvement of the activity of the protein itself present in a microorganism due to mutation so as to achieve effects beyond the endogenous functions, and/or improvement in endogenous gene activity of the protein present in the microorganism, amplification of the endogenous gene by internal or external factors, increase in the gene copy number, increase in the activity by additional introduction of a foreign gene or replacement or modification of a promoter, but are not limited thereto.

The increase in the gene copy number may be, but is not particularly limited to, performed by operably linking the gene to a vector or by integrating it into the host cell genome. Specifically, the copy number of the polynucleotide in the host cell genome may be increased by introducing into the host cell the vector which is operably linked to the polynucleotide encoding the protein of the present invention and replicates and functions independently of the host cell, or by introducing into the host cell the vector which is operably linked to the polynucleotide and is able to integrate the polynucleotide into the host cell genome.

As used herein, "modification of the expression regulatory sequence for increasing the polynucleotide expression" may be, but is not particularly limited to, done by inducing a modification on the expression regulatory conservative substitution of nucleotide sequence, or a combination thereof in order to further enhance the activity of expression regulatory sequence, or by replacing the expression regulatory sequence with a nucleotide sequence having stronger activity. The expression regulatory sequence includes, but is not particularly limited to, a promoter, an operator sequence, a sequence coding for a ribosome-binding site, and a sequence regulating the termination of transcription and translation.

As used herein, the replacement or modification of a promoter, although not particularly limited thereto, may be performed by replacement or modification with a stronger promoter than the original promoter. A strong heterologous promoter instead of the original promoter may be linked upstream of the polynucleotide expression unit, and examples of the strong promoter may include a CJ7 promoter, a lysCP1 promoter, an EF-Tu promoter, a groEL promoter, an aceA or aceB promoter, and specifically, a *Corynebacterium*-derived promoter, lysCP1 promoter or CJ7 promoter is operably linked to the polynucleotide encoding the enzyme so that its expression rate may be increased. Here, the lysCP1 promoter is a promoter improved through nucleotide sequence substitution of the promoter region of the polynucleotide encoding aspartate kinase and aspartate semialdehyde dehydrogenase (WO 2009/086689). Further, CJ7 promoter is a strong promoter derived from *Corynebacterium ammoniagenes* (Korean Patent No. 0620092 and WO 2006/065095).

Furthermore, modification of a polynucleotide sequence on chromosome, although not particularly limited thereto, may be performed, by inducing a mutation on the expression regulatory sequence through deletion, insertion, non-conservative or conservative substitution of polynucleotide sequence, or a combination thereof in order to further enhance the activity of the polynucleotide sequence, or by replacing the sequence with a polynucleotide sequence which is modified to have stronger activity.

As used herein, the term, "vector" refers to a DMA construct including a nucleotide sequence encoding the desired, protein, which is operably linked to an appropriate expression regulatory sequence to express the desired protein in a suitable host cell. The regulatory sequence may include a promoter that can initiate transcription, an optional operator sequence for regulating the transcription, a sequence encoding a suitable mRNA ribosome binding site, and a sequence regulating the termination of transcription and translation. After the vector is introduced into the suitable host cell, it may replicate or function independently of the host genome, and may be integrated into the genome itself.

The vector used in the present invention is not particularly limited, as long as it is able to replicate in the host cell, and any vector known in the art may be used. Examples of conventional vectors may include a natural or recombinant plasmid, cosmid, virus and bacteriophage. For instance, pWE15, M13, λMBL3, λMBL4, λIXII, λASHII, λAPII, λt10, λt11, Charon4A, and Charon21A may be used as a phage vector or cosmid vector. pBR type, pUC type, pBluescriptII type, pGEM type, pTZ type, pCL type and pET type may be used as a plasmid vector. A vector usable in the present invention is not particularly limited, and any known expression vector may be used. Preferably, pDZ, pACYC177, pACYC184, pCL, pECCG117, pUC19, pBR322, pMW118, or pCC1BAC vector may be used.

Further, the polynucleotide encoding the desired endogenous protein in the chromosome can be replaced by a mutated polynucleotide using a vector for bacterial chromosomal insertion. The insertion of the polynucleotide into the chromosome may be performed by any method known in the art, for example, homologous recombination. Since the vector of the present invention may be inserted into the chromosome by homologous recombination, it may further include a selection marker to confirm chromosomal insertion. The selection marker is to select cells that are transformed with the vector, that is, to confirm insertion of the desired polynucleotide, and the selection marker may include markers providing selectable phenotypes, such as drug resistance, auxotrophy, resistance to cytotoxic agents, or surface protein expression. Only cells expressing the selection marker are able to survive or to show different phenotypes under the environment treated with the selective agent, and thus the transformed cells may be selected.

As used herein, the term "transformation" means the introduction of a vector including a polynucleotide encoding a target protein into a host cell in such a way that the protein encoded, by the polynucleotide is expressed in the host cell. As long as the transformed polynucleotide can be expressed in the host cell, it can be either integrated into and placed in the chromosome of the host cell, or exist extrachromosomally. Further, the polynucleotide includes DNA and RNA encoding the target protein. The polynucleotide may be introduced in any form, as long as it can be introduced into the host cell and expressed therein. For example, the polynucleotide may be introduced into the host cell in the form of an expression cassette, which is a gene construct including all elements required for its autonomous expression. Typically, the expression cassette includes a promoter operably linked to the polynucleotide, transcriptional termination signals, ribosome binding sites, or translation termination signals. The expression cassette may be in the form of a self-replicable expression vector. Also, the polynucleotide as it is may be introduced into the host cell and operably linked to sequences required for expression in the host cell.

Further, as used herein, the term "operably linked" means a functional linkage between a polynucleotide sequence encoding the desired protein of the present invention and a promoter sequence which initiates and mediates transcription of the polynucleotide sequence.

Further, the microorganism having diamine productivity may be a microorganism, in which the diamine acetyltransferase activity is weakened compared to the endogenous activity, in order to increase diamine production.

As used herein, the term "diamine acetyltransferase" is an enzyme catalyzing transfer of an acetyl group from acetyl-CoA to diamine, and it may be exemplified by Corynebacterium glutamicum NCgl1469 or E. coli SpeG, but its name may differ depending on the species of a microorganism having diamine productivity. NCgl1469 may have an amino acid sequence of SEQ ID NO: 12 or 13, and SpeG may have an amino acid sequence of SEQ ID NO: 14, but the sequence may differ depending on the species of the microorganism. The protein may have an amino acid sequence having 80% or higher, preferably 90% or higher, or more preferably 95% or higher, or particularly preferably 97% or higher homology therewith, as long as it has the diamine acetyltransferase activity.

Since the diamine acetyltransferase converts diamine to acetyl-diamine (e.g., N-Ac-putrescine or N-Ac-cadaverine), diamine productivity may be increased by weakening its activity, compared to the endogenous activity.

As used herein, the term "endogenous activity" refers to activity of the protein that the original microorganism possesses in its native or undenatured state, and "modified to have weakened activity, compared to the endogenous activity" means that activity of the protein is further weakened compared to the activity of the corresponding protein that the original microorganism possesses in the native or undenatured state.

The weakening of the protein activity means that the protein activity is reduced, compared to a non-modified strain, or the activity is eliminated. It is possible to apply a method well known in the art to the weakening of the protein activity.

Examples of the method may include a method of replacing the gene encoding the protein on the chromosome by a gene that is mutated to reduce the enzyme activity or to eliminate the protein activity, a method of introducing a mutation into the expression regulatory sequence of the gene encoding the protein on the chromosome, a method of replacing the expression regulatory sequence of the gene encoding the protein by a sequence having weaker activity, a method of deleting a part or an entire of the gene encoding the protein on the chromosome, a method of introducing antisense oligonucleotide that complementarily binds to a transcript of the gene on the chromosome to inhibit translation of mRNA to the protein, a method of artificially adding a sequence complementary to SD sequence at upstream of SD sequence of the gene encoding the protein to form a secondary structure, thereby preventing access of the ribosomal subunits, and a reverse transcription engineering (RTE) method of adding a promoter for reverse transcription at 3'-terminus of open reading frame (ORF) of the corresponding sequence, and combinations thereof, but are not particularly limited thereto.

In detail, a partial or full deletion of the gene encoding the protein may be done by introducing a vector for chromosomal insertion into a microorganism, thereby substituting the polynucleotide encoding an endogenous target protein on chromosome with a polynucleotide having a partial deletion or a marker gene. The "partial" may vary depending on the type of polynucleotide, but specifically refers to 1 to 300, preferably 1 to 100, and more preferably 1 to 50 nucleotides.

Meanwhile, the microorganism of the present invention is a microorganism having diamine productivity, and includes a prokaryotic microorganism expressing the protein having the amino acid sequence of SEQ ID NO: 6, and examples thereof may include microorganisms belonging to *Escherichia*, sp., *Shigella* sp., *Citrobacter* sp., *Salmonella* sp., *Enterobacter* sp., *Yersinia* sp., *Klebsiella* sp., *Erwinia* sp., *Corynebacterium* sp., *Brevibacterium* sp., *Lactobacillus* sp., *Selenomanas* sp., *Vibrio* sp., *Pseudomonas* sp., *Streptomyces* sp., *Arcanobacterium* sp., *Alcaligenes* sp. or the like, but are not limited thereto. The microorganism of the present invention is specifically a microorganism belonging to *Coryne-* bacterium sp. or *Escherichia* sp., and more specifically, *Corynebacterium glutamicum* or *Escherichia coli*, but is not limited thereto.

A specific example may be a microorganism prepared by deleting NCgl2522, which is a protein having putrescine export activity, from a *Corynebacterium glutamicum* ATCC13032-based putrescine-producing strain KCCM11240P (Korean Patent Publication No. 2013-0082478) and then introducing ARCH_0271 into the transposon gene. Therefore, this microorganism KCCM11240P ΔNCgl2522 Tn:P(cj7)-ARCH_0271 is designated as CC01-0758, and deposited under the Budapest Treaty to the Korean Culture Center of Microorganisms (KCCM) on Nov. 15, 2013, with Accession No. KCCM11476P.

In another aspect, the present invention provides a method of producing diamine, comprising: (i) culturing the microorganism having putrescine diamine, in which activity of the protein having the amino acid sequence of SEQ ID NO: 6 or 42% or higher sequence homology therewith is introduced or enhanced, so as to obtain a cell culture; and (ii) recovering diamine from the cultured microorganism or the cell culture.

The diamine, the protein having the amino acid sequence of SEQ ID NO: 6 or the protein having the amino acid sequence having 42% or higher sequence homology therewith, the introduction of the protein activity, the enhancement of the protein activity, the diamine, and the microorganism having diamine productivity are the same as described above.

In the method, the step of culturing the microorganism may be, although not particularly limited to, preferably performed by batch culture, continuous culture, and fed-batch culture known in the art. In this regard, the culture conditions are not particularly limited, but an optimal pH (e.g., pH 5 to 9, preferably pH 6 to 8, and most preferably pH 6.8) may be maintained by using a basic chemical (e.g., sodium hydroxide, potassium hydroxide or ammonia) or acidic chemical (e.g., phosphoric acid or sulfuric acid). Also, an aerobic condition may be maintained by adding oxygen or oxygen-containing gas mixture to a cell culture. The culture temperature may be maintained at 20 to 45° C., and preferably at 25 to 40° C., and the cultivation may be performed for about 10 to 160 hours.

Furthermore, a medium to be used for culture may include sugar and carbohydrate (e.g., glucose, sucrose, lactose, fructose, maltose, molasses, starch and cellulose), oil and fat (e.g., soybean oil, sunflower seed oil, peanut oil and coconut oil), fatty acid (e.g., palmitic acid, stearic acid and linoleic acid), alcohol (e.g., glycerol and ethanol), and organic acid (e.g., acetic acid) individually or in combination as a carbon source; nitrogen-containing organic compound (e.g., peptone, yeast extract, meat juice, malt extract, corn solution, soybean meal powder and urea), or inorganic compound (e.g., ammonium sulfate, ammonium chloride, ammonium phosphate, ammonium carbonate, and ammonium nitrate) individually or in combination as a nitrogen source potassium dihydrogen phosphate, dipotassium phosphate, or sodium-containing salt corresponding thereto individually or in combination as a phosphorus source; other essential growth-stimulating substances including metal salts (e.g., magnesium sulfate or iron sulfate), amino acids, and vitamins. In the present invention, the medium may be used as a synonym for the culture liquid.

As used herein, the term "cell culture" is a material obtained by culturing a microorganism, and includes the medium, the microorganism cultured, and substances released from the microorganism cultured. For example, a nutrient supply source required for cell culture, such as minerals, amino acids, vitamins, nucleic acids and/or other components generally contained in culture medium (or culture liquid) in addition to the carbon source, and the nitrogen source may be included. Further, a desired substance or an enzyme produced/secreted by the cells may be included.

Since diamine produced by culture may be secreted into the medium or remain in the cells, the cell culture may include diamine that is produced by culturing the microorganism.

The method of recovering putrescine produced in the culturing step of the present invention may be carried out, for example, using a suitable method known in the art according to a culturing method, for example, batch culture, continuous culture, or fed-batch culture, thereby collecting the desired amino acids from the culture liquid.

Advantageous Effects

In the present invention, it is demonstrated that *Arcanobacterium haemolyticum*-derived ARCH_0271 protein is a protein having diamine export activity, and putrescine export activity can be enhanced by introducing this protein activity into *Corynebacterium* sp. microorganism which has a putrescine synthetic pathway, but low putrescine export activity. It is also demonstrated that the production of putrescine and cadaverine can be increased at the same time by introducing this protein activity into *E. coli* which has synthetic pathways of putrescine and cadaverine. Accordingly, diamine can be effectively produced by applying *Arcanobacterium haemolyticum*-derived ARCH_0271 protein to a microorganism having diamine productivity.

MODE FOR INVENTION

Hereinafter, the present invention will be described in more detail, with reference to Examples. However, these Examples are for illustrative purposes only, and the invention is not intended to be limited by these Examples.

Reference Example 1. Preparation of *Corynebacterium* sp. Microorganism Having Putrescine Productivity It was confirmed that putrescine production was reduced when NCgl2522, a permease belonging to major facilitator super family (MFS), was deleted in a *Corynebacterium glutamicum* ATCC13032-based putrescine-producing strain KCCM11240P (Korean Patent Publication NO. 2013-0032478) and a *Corynebacterium glutamicum* ATCC13869-based putrescine-producing strain DAB12-a ΔNCgl1469 (argF deletion, NCgl1221 deletion, *E. coli* speC introduction, arg operon promoter substitution, NCgl1469 deletion; designated as DAB12-b, Korean Patent Publication NO. 2013-0082478) as *Corynebacterium* sp. microorganisms having putrescine productivity.

It was also confirmed that putrescine was produced in a high yield in *Corynebacterium glutamicum* strains prepared by additional introduction of NCgl2522 gene into the transposon in KCCM11240P or DAB12-b, or by substitution of NCgl2522 promoter on the chromosome with cj7 promoter to enhance NCgl2522 activity. Further, the intracellular amount of putrescine was measured in the strain in which NCgl2522 expression was enhanced, and as a result, a smaller amount of putrescine was observed, compared to that of a control group. It is indicating that NCgl2522 has an ability to export putrescine.

In detail, based, on the nucleotide sequence of the gene encoding NCgl2522 of *Corynebacterium glutamicum* ATCC13032, a pair of primers of SEQ ID NOS: 1 and 2 for obtaining a homologous recombination fragment of the N-terminal region of NCgl2522 and a pair of primers of SEQ ID NOS: 3 and 4 for obtaining a homologous recombination fragment of the C-terminal region of NCgl2522 were used as in the following Table 1.

TABLE 1

| Primer | Sequence (5'→3') |
| --- | --- |
| NCgl2522-del-F1_BamHI (SEQ ID NO: 1) | CGGGATCCCACGCCTGTCTGGTCGC |
| NCgl2522-del-R1_SalI (SEQ ID NO: 2) | ACGCGTCGACGGATCGTAACTGTAACGAATGG |
| NCgl2522-del-F2_SalI (SEQ ID NO: 3) | ACGCGTCGACCGCGTGCATCTTTGGACAC |
| NCgl2522-del-R2_XbaI (SEQ ID NO: 4) | CTAGTCTAGAGAGCTGCACCAGGTAGACG |

PGR was performed using the genomic DNA of *Corynebacterium glutamicum* ATCC13032 as a template and two pairs of primers so as to amplify PGR fragments of the N-terminal and C-terminal regions, respectively. These PCR fragments were electrophoresed to obtain the desired fragments. At this time, PCR reaction was carried out for 30 cycles of denaturation for 30 seconds at 95° C., annealing for 30 seconds at 55° C., and extension for 30 seconds at 72° C. The fragment of the N-terminal region thus obtained was treated with restriction enzymes, BamHI and SalI, and the fragment of the C-terminal region thus obtained was treated with restriction enzymes, SalI and XbaI. The fragments thus treated were cloned into the pDZ vector treated with restriction enzymes, BamHI and XbaI, so as to construct a plasmid pDZ-1'NCgl2522(K/O).

The plasmid pDZ-1'NCgl2522(K/O) was introduced into *Corynebacterium glutamicum* KCCM11240P by electroporation, so as to obtain a transformant. Then, the transformant was plated and cultured on BHIS plate (37 g/l of Braine heart, infusion, 91 g/l of sorbitol, and 2% agar) containing kanamycin (25 µg/ml) and X-gal (5-bromo-4-chloro-3-indolin-D-galactoside) for colony formation. From the colonies thus formed, blue-colored colonies were selected as the strain introduced with the plasmid pDZ-1'NCgl2522(K/O).

The selected strains were cultured with shaking in CM medium (10 g/l of glucose, 10 g/l of polypeptone, 5 g/l of yeast extract, 5 g/l of beef extract, 2.5 g/l of NaCl, and 2 g/l of urea, pH 6.8) at 30° C. for 8 hours. Subsequently, each cell culture was serially diluted from $10^{-4}$ to $10^{-10}$. Then, the diluted samples were plated and cultured on an X-gal-containing solid medium for colony formation. From the colonies thus formed, the white colonies which appeared at relatively low frequency were selected to finally obtain a *Corynebacterium glutamicum* strain in which the gene encoding NCgl2522 was deleted and putrescine productivity was weakened. The *Corynebacterium glutamicum* strain in which putrescine export activity was weakened was designated as KCCM11240P ΔNCgl2522.

In the same manner, PCR was performed using the genomic DNA of *Corynebacterium glutamicum* ATCC13869 as a template and two pairs of primers given in Table 1 so as to construct a plasmid pDZ-2'NCgl2522(K/O) by the above described method. A *Corynebacterium glutamicum* strain, in which the gene encoding NCgl2522 of DAB12-b strain was deleted using the vector according to the above described method to weaken putrescine productivity, was constructed. This *Corynebacterium glutamicum* strain having weakened putrescine export activity was designated as DAB12-b ΔNCgl2522.

Example 1. Selection of *Arcanobacterium haemolyticum* ARCH 0271

As confirmed in Reference Example 1, the NCgl2522 membrane protein was found to function to export putrescine. Therefore, based on the amino acid sequence of NCgl2522, the present inventors examine genes having homology therewith other than genes of *Corynebacterium* sp. using BlastP program of National Center for Biotechnology Information (NCBI, www.ncbi.nlm.nih.gov), and as a result, they acquired a nucleotide sequence (SEQ ID NO: 5) and an amino acid sequence (SEQ ID NO: 6) of ARCH_0271 of *Arcanobacterium haemolyticum* DSM 20595, which has 56% homology therewith. Among the membrane proteins having a homology with the amino acid sequence of NCgl2522, which are found in other species than *Corynebacterium* sp., the amino acid sequence of ARCH_0271 is phylogenetically closest to the amino acid sequence of NCgl2522.

In the same manner, the nucleotide sequence (SEQ ID NO: 22) and amino acid sequence (SEQ ID NO: 23) of QWA_00075 derived from *Alcaligenes faecalis* subsp. *faecalis* NCIB 8687, which shows 41% homology with the amino acid sequence of NCgl2522, and the nucleotide sequence (SEQ ID NO: 25) and amino acid sequence (SEQ ID NO: 26) of SMD_2351 derived from *Stenotrophomonas maltophilia* D457, which shows 52% homology with the amino acid sequence of NCgl2522, were obtained. The amino acid sequence of QWA_00075 and the amino acid sequence of SMD_2351 show 42% and 47% homology with the amino acid sequence of ARCH_0271, respectively, as shown in the following Table 2.

TABLE 2

| Comparison of amino acid sequence homology | | | |
| --- | --- | --- | --- |
| | ARCH_0271 | QWA_00075 | SMD_2351 |
| NCgl2522 | 56% | 41% | 52% |
| ARCH_0271 | | 42% | 47% |

Meanwhile, microorganisms having genes showing homology with NCgl2522, and homology thereof are given in the following Table 3.

TABLE 3

| Species | Homology |
| --- | --- |
| *Acidovorax citrulli* AAC00-1 | 47% |
| *Actinomyces* sp. oral taxon 181 | 53% |
| *Actinomyces* sp. ph3 | 54% |
| *Actinomyces* sp. S6-Spd3 | 53% |
| *Actinosynnema mirum* | 53% |
| *Actinosynnema mirum* DSM 43827 | 53% |
| *Alcaligenes faecalis* subsp. *faecalis* NCIB 8687 | 41% |
| alpha proteobacterium LLX12A | 52% |
| *Arcanobacterium haemolyticum* | 56% |

TABLE 3-continued

| Species | Homology |
|---|---|
| Arcanobacterium haemolyticum DSM 20595 | 56% |
| Arsenophonus nasoniae | 44% |
| Brachybacterium paraconglomeratum | 52% |
| Brachybacterium paraconglomeratum LC44 | 52% |
| Bradyrhizobium sp. BTAi1 | 43% |
| Citricoccus sp. CH26A | 50% |
| Citrobacter freundii 4_7_47CFAA | 53% |
| Dermabacter hominis 1368 | 50% |
| Dermabacter sp. HFH0086 | 51% |
| Dietzia sp. UCD-THP | 52% |
| Enterobacteriaceae bacterium 9_2_54FAA | 41% |
| Erwinia amylovora ATCC 49946 | 47% |
| Granulicoccus phenolivorans | 55% |
| Hafnia alvei ATCC 51873 | 41% |
| Klebsiella pneumoniae | 53% |
| Micrococcus luteus | 52% |
| Micromonospora sp. ATCC 39149 | 53% |
| Mycobacterium chubuense | 39% |
| Mycobacterium gilvum | 38% |
| Mycobacterium neoaurum | 39% |
| Mycobacterium rufum | 39% |
| Nesterenkonia alba | 48% |
| Nesterenkonia sp. F | 51% |
| Nocardia rhamnosiphila | 40% |
| Nocardiopsis dassonvillei | 58% |
| Nocardiopsis dassonvillei subsp. dassonvillei DSM 43111 | 57% |
| Nocardiopsis kunsanensis | 52% |
| Nocardiopsis sp. CNS639 | 57% |
| Nocardiopsis synnemataformans | 57% |
| Ochrobactrum anthropi ATCC 49188 | 46% |
| Pectobacterium atrosepticum SCRI1043 | 46% |
| Providencia alcalifaciens DSM 30120 | 40% |
| Pseudomonas aeruginosa | 53% |
| Pseudomonas aeruginosa C3719 | 46% |
| Pseudomonas geniculata | 53% |
| Rahnella aquatilis HX2 | 40% |
| Rhodococcus | 40% |
| Rhodococcus fascians | 55% |
| Rhodococcus sp. AW25M09 | 42% |
| Rhodococcus sp. JVH1 | 40% |
| Rhodococcus triatomae | 37% |
| Rhodococcus wratislaviensis NBRC 100605 | 40% |
| Salinispora | 52% |
| Salinispora arenicola | 52% |
| Salinispora pacifica | 53% |
| Salinispora tropica CNB-440 | 51% |
| Sanguibacter keddieii DSM 10542 | 52% |
| Serratia marcescens | 44% |
| Sphingobium chinhatense | 53% |
| Stenotrophomonas maltophilia | 54% |
| Stenotrophomonas maltophilia D457 | 52% |
| Stenotrophomonas sp. RIT309 | 52% |
| Stenotrophomonas sp. SKA14 | 53% |
| Streptococcus anginosus | 52% |
| Streptococcus anginosus CCUG 39159 | 51% |
| Streptomyces | 52% |
| Streptomyces albidoflavus | 54% |
| Streptomyces alboviridis | 52% |
| Streptomyces albus | 55% |
| Streptomyces albus J1074] | 57% |
| Streptomyces atroolivaceus | 53% |
| Streptomyces baarnensis | 51% |
| Streptomyces californicus | 52% |
| Streptomyces cyaneofuscatus | 53% |
| Streptomyces floridae | 52% |
| Streptomyces fulvissimus | 51% |
| Streptomyces globisporus | 52% |
| Streptomyces griseus | 57% |
| Streptomyces mediolani | 55% |
| Streptomyces sp. AA0539 | 48% |
| Streptomyces sp. CcalMP-8W | 52% |
| Streptomyces sp. CNB091 | 55% |
| Streptomyces sp. NRRL B-1381 | 52% |
| Streptomyces sp. NRRL B-3253 | 57% |
| Streptomyces sp. NRRL F-2890 | 49% |
| Streptomyces sp. NRRL F-5527 | 52% |
| Streptomyces sp. NRRL F-5702 | 52% |
| Streptomyces sp. NRRL S-623 | 52% |
| Streptomyces sp. PVA 94-07 | 57% |
| Streptomyces sp. S4 | 54% |
| Streptomyces sp. ScaeMP-e10 | 51% |
| Streptomyces sp. SM8 | 54% |
| Streptomyces sp. W007 | 54% |
| Streptomyces wadayamensis | 54% |
| Tsukamurella paurometabola | 38% |
| Turicella otitidis | 56% |
| Turicella otitidis ATCC 51513 | 56% |
| Xenorhabdus nematophila ATCC 19061 | 42% |
| Yaniella halotolerans | 61% |
| Yersinia enterocolitica | 41% |

Example 2. Fermentation of Putrescine by Introduction of Protein Having Putrescine Export Activity into Putrescine-Producing Strain Derived from *Corynebacterium* sp.

<2-1> Introduction of ARCH_0271, QWA_00075, or SMD_2351 into Transposon Gene in Chromosome of ATCC13032-Based Putrescine-Producing Strain In order to examine whether chromosomal insertion of ARCH_0271, QWA_00075 or SMD_2351 gene affects putrescine export in KCCM11240P ΔNCgl2522 having reduced putrescine export activity which was prepared in Reference Example 1, ARCH_0271, QWA_00075, or SMD_2351 was introduced into a transposon gene by the following method.

As a vector for transformation, which allows a gene insertion into the chromosome using a transposon gene of *Corynebacterium* sp. microorganism, pDZTn (WO 2009/125992) was used, and cj7 (WO 2006/65095) was used as a promoter.

Based on the nucleotide sequence of *Arcanobacterium haemolyticum* DSM 20595, ARCH_0271 gene was synthesized by optimizing the nucleotide sequence (SEQ ID NO: 7) for codon usage of *Corynebacterium glutamicum*. In the same manner, QWA_00075 derived from *Alcaligenes faecalis* subsp. *faecalis* NCIB 8687 and SMD_2351 derived from *Stenotrophomonas maltophilia* D457 were also synthesized by optimizing the nucleotide sequences (SEQ ID NO: 24, and SEQ ID NO: 27) for codon usage of *Corynebacterium glutamicum*, respectively. The genes synthesized were obtained as genes cloned into pGEM B1.

The plasmids thus obtained were designated as pGEM B1-ARCH_0271, pGEM B1-QWA_00075, and pGEM B1-SMD_2351, respectively.

A gene fragment of about 1.51 kb, 1.53 kb, or 1.53 kb was amplified using pGEM B1-ARCH_0271 m pGEM B1-QWA_00075, or pGEM B1-SMD_2351 plasmid as a template and a pair of primers of SEQ ID NOs. 10 and 11, SEQ ID NOs. 28 and 29, or SEQ ID NOs. 30 and 31 (See Table 4), respectively. At this time, PCR reaction was carried out for 30 cycles of denaturation for 30 seconds at 95° C., annealing for 30 seconds at 55° C., and extension for 1 minute and 30 seconds at 72° C. Next, these PGR products were electrophoresed on a 0.8% agarose gel to elute and purify each band of the desired size.

Further, the cj7 promoter region was obtained by carrying out PCR for 30 cycles of denaturation for 30 seconds at 95° C., annealing for 30 seconds at 55° C., and extension for 30 seconds at 72° C. using p117-Pcj7-gfp as a template and a pair of primers of SEQ ID NOs. 8 and 9 (See Table 4). A fragment of the cj7 promoter gene was electrophoresed on a 0.8% agarose gel to elute and purify a band of the desired size.

TABLE 4

| Primer | Sequence (5'→3') |
|---|---|
| CJ7-F (SEQ ID NO: 8) | TGTCGGGCCCACTAGT AGAAACATCCCAGCGCTACTAATA |
| CJ7-R (SEQ ID NO: 9) | AGTGTTTCCTTTCGTTGGGTACG |
| ARCH_0271-F (SEQ ID NO: 10) | CAACGAAAGGAAACACT ATGCCAGACGTGTCCTCC |
| ARCH_0271-R (SEQ ID NO: 11) | GAATGAGTTCCTCGAG TTATTCGTGTGCATATGC |
| QWA_00075-F (SEQ ID NO: 28) | CAACGAAAGGAAACACT ATGTTGCACTCCCCCACCC |
| QWA_00075-R (SEQ ID NO: 29) | GAATGAGTTCCTCGAG TTAATCAGCATGGGAGCGGCC |
| SMD_2351-F (SEQ ID NO: 30) | CAACGAAAGGAAACACT ATGCCAGCAGCGCATTCAAATAG |
| SMD_2351-R (SEQ ID NO: 31) | GAATGAGTTCCTCGAG TTAGTGCTGAGTTGGATAGGCAG | pDZTn vector was digested with XhoI, and fusion cloning of each PGR product obtained above was performed. In-Fusion®HD Cloning Kit (Clontech) was used in the fusion cloning. The resulting plasmids were designated as pDZTn-P(cj7)-ARCH_0271, pDZTn-P (cj7)-QWA_00075, and pDZTn-P(cj7)-SMD_2351, respectively.

Each of the three plasmids pDZTn-P(cj7)-ARCH_0271, pDZTn-P(cj7)-QWA_00075, and pDZTn-P(cj7)-SMD_2351 was introduced into *Corynebacterium glutamicum* KCCM11240P ΔNCgl2522 having reduced putrescine export activity described in Reference Example 1 by electroporation to obtain transformants. The transformants were cultured with shaking in CM medium (10 g/l of glucose, 10 g/l of polypeptone, 5 g/l of yeast extract, 5 g/l of beef extract, 2.5 g/l of NaCl, and 2 g/l of urea, pH 6.8) (30° C. for 8 hours). Subsequently, each cell culture was serially diluted from $10^{-4}$ to $10^{-10}$. Then, the diluted samples were plated and cultured on an X-gal-containing solid medium for colony formation.

From the colonies formed, the white colonies which appeared at relatively low frequency were selected to finally obtain strains in which the gene encoding ARCH_0271, QWA_00075 or SMD_2351 was introduced by secondary crossover. The strains finally selected were subjected to PCR using a pair of primers of SEQ ID NOs. 8 and 11, SEQ ID NOs. 8 and 29, or SEQ ID NOs. 8 and 31 to confirm introduction of the gene encoding ARCH_0271, QWA_00075 or SMD_2351. These *Corynebacterium glutamicum* mutant strain were designated as KCCM11240P ΔNCgl2522 Tn:P(cj7)-ARCH_0271, KCCM11240P ΔNCgl2522 Tn:P(cj7)-QWA_00075, and KCCM11240P ΔNCgl2522 Tn:P(cj7)-SMD_2351, respectively.

<2-2> Introduction of ARCH_0271, QWA_00075, or SMD_2351 into Transposon Gene in Chromosome of ATCC13869-Based Putrescine-Producing Strain In order to examine whether the chromosomal insertion of ARCH_0271 gene affects putrescine export in DAB12-b ΔNCgl2522 having reduced putrescine export activity which was prepared in Reference Example 1, pDZTn-P (cj7)-ARCH_0271, pDZTn-P(cj7)-QWA_00075, or pDZTn-P (cj7)-SMD_2351 prepared above was introduced into *Corynebacterium glutamicum* DAB12-b ΔNCgl2522 and strains are confirmed introduction of ARCH_0271, QWA_00075 or SMD_2351 into the transposon gene in the same manner as in Example <2-1>.

*Corynebacterium glutamicum* mutant strains thus selected were designated as DAB12-b ΔNCgl2522 Tn:P(cj7)-ARCH_0271, DAB12-b ΔNCgl2522 Tn:P(cj7)-QWA_00075, and DAB12-b ΔNCgl2522 Tn:P(cj7)-SMD_2351, respectively.

<2-3> Evaluation of Putrescine Productivity of *Corynebacterium* sp.-derived Putrescine-Producing Strain Introduced with ARCH_0271, QWA_00075 or SMD_2351

In order to confirm the effect of ARCH_0271 introduction on putrescine productivity in the putrescine-producing strain, putrescine productivities of the *Corynebacterium glutamicum* mutant strains prepared in Examples <2-1> and <2-2> were compared.

In detail, 10 types of *Corynebacterium glutamicum* mutants (KCCM11240P; KCCM11240P ΔNCgl2522; KCCM11240P ΔNCgl2522 Tn:P(cj7)-ARCH_0271; KCCM11240P ΔNCgl2522 Tn: P(cj7)-QWA_00075; KCCM11240P ΔNCgl2522 Tn:P(cj7)-SMD_2351; DAB12-b; DAB12-b ΔNCgl2522; DAB12-b ΔNCgl2522 Tn:P(cj7)-ARCH_0271; DAB12-b ANCgl2522 Tn:P(cj7)-QWA_00075, and DAB12-b ΔNCgl2522 Tn:P(cj7)-SMD_2351) were plated on 1 mM arginine-containing CM plate media (1% glucose, 1% polypeptone, 0.5% yeast extract, 0.5% beef extract, 0.25% NaCl, 0.2% urea, 100 μl of 50% NaOH, and 2% agar, pH 6.8, based on 1 L), and cultured at 30° C. for 24 hours, respectively. 1 platinum loop of each strain thus cultured was inoculated in 25 ml of titer medium (8% Glucose, 0.25% soybean protein, 0.50% corn steep solids, 4% $(NH_4)_2SO_4$, 0.1% $KH_2PO_4$, 0.05% $MgSO_4 \cdot 7H_2O$, 0.15% urea, 100 μg of biotin, 3 mg of thiamine hydrochloride, 3 mg of calcium-pantothenic acid, 3 mg of nicotinamide, and 5% $CaCO_3$, pH 7.0, based on 1 L), and then cultured with shaking at 30° C. and 200 rpm for 98 hours, 1 mM arginine was added to all media for culturing the strains. The putrescine concentration in each cell culture was measured, and the results are shown in the following Table 5.

TABLE 5

| Strain | Putrescine (g/L) |
|---|---|
| KCCM 11240P | 12.4 |
| KCCM 11240P ΔNCgl2522 | 1.9 |
| KCCM 11240P ΔNCgl2522 Tn:P(cj7)- ARCH_0271 | 17.7 |
| KCCM 11240P ΔNCgl2522 Tn:P(cj7)- QWA_00075 | 4.1 |
| KCCM 11240P ΔNCgl2522 Tn:P(cj7)- SMD_2351 | 3.5 |
| DAB12-b | 13.1 |
| DAB12-b ΔNCgl2522 | 0.5 |
| DAB12-b ΔNCgl2522 Tn:P(cj7)- ARCH_0271 | 17.5 |
| DAB12-b ΔNCgl2522 Tn:P(cj7)- QWA_00075 | 5 |
| DAB12-b ΔNCgl2522 Tn:P(cj7)- SMD_2351 | 4.1 |

As shown in Table 5, putrescine production was found to be increased in both 2 types of the ARCH_0271-introduced *Corynebacterium glutamicum* mutant strains. Further, putrescine production was found to be increased in the QWA_00075 or SMD_2351-introduced strain, compared to the parent strain, KCCM 11240P ΔNCgl2522 or DAB12-b ΔNCgl2522. It is indicating that QWA_00075 or SMD_2351 has putrescine export activity.

Example 3. Fermentation of Cadaverine by ARCH 0271 Introduction and Lysine Decarboxylase Expression in *Corynebacterium* sp.-Derived Lysine-Producing Strain <3-1> Introduction of ARCH_0271 into Transposon Gene in Chromosome of L-Lysine-Producing *Corynebacterium glutamicum* KCCM11016P In order to confirm cadaverine export activity of ARCH_0271 protein, ARCH_0271 gene was introduced into the chromosome of a lysine-producing strain KCCM11016P (this microorganism was deposited at the Korean Culture Center of Microorganisms on Dec. 18, 1995 with Accession No. KFCC10881, and then deposited at the International Depository Authority under Budapest Treaty with Accession No. KCCM11016P, Korean Patent No. 10-0159812). pDZTn-P(cj7)-ARCH_0271 prepared above was introduced into *Corynebacterium glutamicum* KCCM11016P and strain is confirmed introduction of ARCH_0271 into transposon in the same manner as in Example <2-1>.

A *Corynebacterium glutamicum* mutant strain thus selected was designated as KCCM11016P Tn:P(cj7)-ARCH_0271.

<3-2> Introduction of *E. coli*-Derived Lysine Decarboxylase Gene into L-Lysine-Producing Strain Introduced ARCH_0271

The L-lysine-producing strain introduced ARCH_0271, KCCM11016P Tn:P(cj7)-ARCH_0271 which was prepared in Example <3-1> was introduced with *E. coli*-derived lysine decarboxylase gene in a plasmid form for cadaverine production. The nucleotide sequence (SEQ ID NO: 32) and amino acid sequence (SEQ ID NO: 33) of lysine decarboxylase ldcD from *E. coli* were obtained from NCBI data base.

An ldcC gene fragment of about 2.1 kb was obtained by carrying out PCR for 30 cycles of denaturation for 30 seconds at 95° C., annealing for 30 seconds at 52° C., and extension for 2 minutes at 72° C. using the chromosome of *E. coli* W3110 strain as a template and a pair of primers of SEQ ID NOS: 36 and 37 (See Table 6). This product was treated with HindIII and XbaI, and then electrophoresed in a 0.8% agarose gel to elute and purify a band, of the desired size.

Further, the cj7 promoter region was obtained by carrying out PCR for 30 cycles of denaturation for 30 seconds at 95° C., annealing for 30 seconds at 55° C., and extension for 30 seconds at 72° C. using p117-Pcj7-gfp as a template and a pair of primers of SEQ ID NOs. 34 and 35 (See Table 6). A gene fragment of the cj7 promoter gene was treated, with KpnI and HindIII, and then electrophoresed on a 0.8% agarose gel to elute and purify a band of the desired size.

TABLE 6

| Primer for promoter cj7 gene | |
|---|---|
| CJ7-F_KpnI (SEQ ID NO: 34) | CGGGGTACC AGAAACATCCCAGCGCTACTAATA |
| CJ7-R-HindIII (SEQ ID NO: 35) | CCCAAGCTT AGTGTTTCCTTTCGTTGGGTACG |

| Primer for *E. coli* ldcC gene | |
|---|---|
| ldcC-F_HindIII (SEQ ID NO: 36) | CCCAAGCTT AAGCTT ATGAACATCATTGCCATTATGGG (52) |
| ldcC-R_XbaI (SEQ ID NO: 37) | TGCTCTAGA TTATCCCGCCATTTTAGGACTC (53) |

A gene fragment which was obtained by performing electrophoresis of KpnI and XbaI-treated pECCG117 (Biotechnology letters vol 13, No. 10, p, 721-726 (1991)) vector in a 0.8% agarose gel and then eluting and purifying a band of the desired size, the cj7 promoter gene fragment treated with KpnI and HindIII, and the lysine decarboxylase ldcC gene fragment treated with HindIII and XbaI were cloned using T4 DNA ligase (NEB). The *E. coli* ldcC-encoding plasmid obtained by the above experiment was designated as pECCG117-Pcj7-ldcC.

The prepared pECCG117-Pcj7-ldcC vector or pECCG117 vector was introduced into KCCM11016F and KCCM11016P Tn:P(cj7) ARCH_0271 by electroporation, respectively. The transformants were plated on BHIS plate containing 25 μg/ml kanamycin for selection. The selected strains were designated as KCCM11016P pECCG117, KGCM11016P pECCG117-Pcj7-ldcC, KCCM11016P Tn:P(cj7)-ARCH_0271 pECCG117, and KCCM11016P Tn:P(cj7)-ARCH_0271 pECCG117-Pcj7-ldcC, respectively.

<3-3> Evaluation of Cadaverine Productivity of *Corynebacterium* sp.-Derived Lysine-Producing Strain Having Chromosomal Insertion of ARCH_0271 and Lysine Decarboxylase Gene as Plasmid In order to examine whether introduction of ARCH_0271 into the cadaverine-producing strain affects cadaverine production, cadaverine productivity was compared between *Corynebacterium glutamicum* mutant strains prepared in Example <3-2>.

In detail, 4 types of *Corynebacterium glutamicum* mutant strains (KCCM11016P pECCG117; KCCM11016P pECCGH7-Pcj7-ldcC; KCCM11016 P Tn:P(cj7)-ARCH_0271 pECCG117; and KCCM11016P Tn:P(cj7)-ARCH_0271 pECCG117-Pcj7-ldcC) were cultured by the following method, and cadaverine productivity was compared therebetween.

The respective mutant strains were plated on CM plate media (1% glucose, 1% polypeptone, 0.5% yeast extract, 0.5% beef extract, 0.25% NaCl, 0.2% urea, 100 μl of 50% NaOH, and 2% agar, pH 6.8, based on 1 L), and cultured at 30° C. for 24 hours. Each of the strains cultured was inoculated to a 250 ml corner-baffled flask containing 25 ml of seed medium (2% glucose, 1% peptone, 0.5% yeast extract, 0.15% urea, 0.4% $KH_2PO_4$, 0.8% $K_2HPO_4$, 0.05% $MgSO_4$ $7H_2O$, 100 μg of biotin, 1000 μg of thiamine HCl, 2000 μg of calcium-pantothenic acid, and 2000 μg of nicotinamide, pH 7.0, based on 1 L), and cultured with shaking at 30° C. and 200 rpm for 20 hours.

Then, 1 ml of the seed culture was inoculated to a 250 ml corner-baffled flask containing 24 ml of production medium (4% Glucose, 2% $(NK_4)_2SO_4$, 2.5% soybean protein, 5% corn steep solids, 0.3% urea, 0.1% $KH_2PO_4$, 0.05% $MgSO_4$ $7H_2O$, 100 μg of biotin, 1000 μg of thiamine hydrochloride, 2000 μg of calcium-pantothenic acid, 3000 μg of nicotinamide, 0.2 g of leucine, 0.1 g of threonine, 0.1 g of methionine, and 5% $CaCO_3$, pH 7.0, based on 1 L), and then cultured with shaking at 30° C. and 200 rpm for 72 hours.

After culture, cadaverine productivities were measured by HPLC. The concentrations of cadaverine in the cell culture of each strain are given in the following Table 7.

TABLE 7

| Strain | Plasmid | Cadaverine (g/L) |
|---|---|---|
| KCCM11016P | pECCG117 | 0 |
| | pECCG117-Pcj7-ldcC | 2.3 |

TABLE 7-continued

| Strain | Plasmid | Cadaverine (g/L) |
|---|---|---|
| KCCM11016P | pECCG117 | 0 |
| Tn:P(cj7)-ARCH_0271 | pECCG117-Pcj7-ldcC | 2.7 |

As shown in Table 7, cadaverine production was increased in the ARCH_0271-introduced *Corynebacterium glutamicum* mutant strains by more than 17%.

Example 4. Fermentation of Diamine by Introduction of Protein Having Diamine Export, Activity into *E. coli*

<4-1> Preparation of Strain by Introduction of ARCH_0271, QWA_00075, or SMD_2351 into W3110

In order to examine whether expression of *Arcanobacterium haemolyticum* DSM 20595-derived ARCH_0271, *Alcaligenes faecalis*-derived QWA_00075, or *Stenotrophomonas maltophilia*-derived SMD_2351 increases putrescine and cadaverine productions in wild-type *E. coli* strain W3110 having biosynthetic pathway of putrescine and cadaverine, *Corynebacterium* and *E. coli* shuttle vector-based pDZTn-P(cj7)-ARCH_0271, pDZTn-P(cj7)-QWA_00075, or pDZTn-P(cj7)-SMD_2351 was introduced into W3110, respectively.

A 2×TSS solution (Epicentre) was used for transformation into *E. coli*, and the transformant was plated and cultured on LB plate (10 g of Tryptone, 5 g of Yeast extract, 10 g of NaCl, and 2% agar, based on 1 L) containing kanamycin (50 µg/ml) for colony formation. The colonies thus formed were designated as W3110 pDZTn-P(cj7)-ARCH_0271, W3110 pDZTn-P(cj7)-QWA_00075, and W3110 pDZTn-P(cj7)-SMD_2351, respectively.

<4-2> Comparison of Diamine Productivity of *E. coli* Introduced with ARCH_0271, QWA_00075, or SMD_2351

Putrescine and cadaverine productivities of the strains obtained above were examined.

In detail, W3110 and W3110 pDZTn-P(cj7)-ARCH_0271, W3110 pDZTn-P(cj7)-QWA_00075, or W3110 pDZTn-P(cj7)-SMD_2351 were cultured on LB solid media at 37° C. for 24 hours.

Then, each of them was cultured in 25 ml of titration medium (2 g of $(NH_4)_2PO_4$, 6.75 g of $KH_2PO_4$, 0.85 g of citric acid, 0.7 g of $MgSO_4.7H_2O$, 0.5% (v/v) trace element, 10 g of glucose, 3 g of AMS, and 30 g of $CaCO_3$, based on 1 L) at 37° C. for 24 hours. A trace metal solution contained 5 M HCl: 10 g of $FeSO_4.7H_2O$, 2.25 g of $ZnSO_4.7H_2O$, 1 g of $CuSO_4.5H_2O$, 0.5 g of $MnSO_4.5H_2O$, 0.23 g of $Na_2B_4O_7.10H_2O$, 2 g of $CaCl_2.2H_2O$, and 0.1 g of $(NH_4)_6Mo_7O_2.4H_2O$ per 1 liter.

The concentrations of putrescine and cadaverine produced from each cell culture were measured, and the results are given in the following Table 8.

TABLE 8

| Parent strain | Plasmid | Putrescine (mg/L) | Cadaverine (mg/L) |
|---|---|---|---|
| W3110 | (—) | 13 | 5 |
|  | pDZTn-P(cj7)-ARCH_0271 | 51 | 23 |
|  | pDZTn-P(cj7)-QWA_00075 | 72 | 30 |
|  | pDZTn-P(cj7)-SMD_2351 | 37 | 15 |

As shown in Table 8, compared to the parent strain W3110, putrescine and cadaverine productions were remarkably increased, in W3110 pDZTn-P (cj7)-ARCH_0271, W3110 pDZTn-P(cj7)-QWA_00075, or W3110 pDZTn-P(cj7)-SMD_2351 strain which was introduced with ARCH_0271, QWA_00075 or SMD_2351, respectively.

That is, it was confirmed that the amount of diamine produced in cell culture was remarkably increased by enhancing activity of the ARCH_0271, QWA_00075 or SMD_2351 protein having 56%, 41%, or 52% sequence homology with the amino acid sequence of NCgl2522, suggesting that the ability to export diamine such as putrescine and cadaverine can be improved by enhancing activity of CE2495 or the protein having 42% or higher sequence homology therewith.

As such, the present inventors demonstrated that *Corynebacterium glutamicum* having enhanced ARCH_0271 activity prepared by introducing ARCH_0271 into transposon of *Corynebacterium* sp. microorganism KCCM11240P ΔNCgl2522 which has a putrescine synthetic pathway, but a reduced putrescine export activity has enhanced putrescine export activity, thereby producing putrescine in a high yield.

Accordingly, this strain KCCM11240P ΔNCgl2522 Tn:P (cj7)-ARCH_0271 was designated as CC01-0758, and deposited under the Budapest Treaty to the Korean Culture Center of Microorganisms (KCCM) on Nov. 15, 2013, under Accession No. KCCM11476P.

The invention claimed is:

1. A microorganism for producing putrescine, wherein activity of a protein comprising an amino acid sequence having at least 95% identity to SEQ ID NO:23, or SEQ ID NO:26 is introduced or enhanced compared to the endogenous activity.

2. The microorganism according to claim 1, wherein diamine acetyltransferase activity is further weakened compared to the endogenous activity.

3. The microorganism according to claim 2, wherein the diamine acetyltransferase has the amino acid sequence selected from the group consisting of SEQ ID NOS: 12, 13, and 14.

4. The microorganism according to claim 1, wherein the microorganism is a microorganism belonging to genus *Corynebacterium* or genus *Escherichia*.

5. A method of producing putrescine, comprising:
   (i) culturing the microorganism of any one of claims 1, 2, 3, and 4 to obtain a cell culture; and
   (ii) recovering putrescine from the cultured microorganism or the cell culture.

* * * * *

SEQUENCE LISTING

<160> NUMBER OF SEQ ID NOS: 37

<210> SEQ ID NO 1
<211> LENGTH: 25
<212> TYPE: DNA
<213> ORGANISM: Artificial Sequence
<220> FEATURE:
<223> OTHER INFORMATION: NCgl2522-del-F1_BamHI Primer

<400> SEQUENCE: 1
cgggatccca cgcctgtctg gtcgc                25

<210> SEQ ID NO 2
<211> LENGTH: 32

```
<212> TYPE: DNA
<213> ORGANISM: Artificial Sequence
<220> FEATURE:
<223> OTHER INFORMATION: NCgl2522-del-R1_SalI Primer

<400> SEQUENCE: 2
acgcgtcgac ggatcgtaac tgtaacgaat gg                                    32

<210> SEQ ID NO 3
<211> LENGTH: 29
<212> TYPE: DNA
<213> ORGANISM: Artificial Sequence
<220> FEATURE:
<223> OTHER INFORMATION: NCgl2522-del-F2_SalI Primer

<400> SEQUENCE: 3
acgcgtcgac cgcgtgcatc tttggacac                                        29

<210> SEQ ID NO 4
<211> LENGTH: 29
<212> TYPE: DNA
<213> ORGANISM: Artificial Sequence
<220> FEATURE:
<223> OTHER INFORMATION: NCgl2522-del-R2_XbaI Primer

<400> SEQUENCE: 4
ctagtctaga gagctgcacc aggtagacg                                        29

<210> SEQ ID NO 5
<211> LENGTH: 1521
<212> TYPE: DNA
<213> ORGANISM: Arcanobacterium haemolyticum

<400> SEQUENCE: 5
atgcctgacg tttcttcttc cccggtttcc ggagtggttc ccgcaccgca tcccgcacct        60
tcctccgcca tgtctgcccg ccgcaagtgg ctgttccttg gcgtgcttag ttctggcctg       120
ttcttggttg gtgtggataa ttcggtgctt tacacggctc ttcctgagct gcgccgcgtg       180
cttcacacaa cggagctcca gggcctgtgg attattaacg cttacccgct agtcctcgcg       240
ggtctccttc tgggcactgg cacgctaggc gataagatcg gccatcgccg tatgtggatg       300
attggcctgg tggtgttcat gttttgcgtcg ctgggtgcgg cgttcgcgcc gggcccgtgg       360
tggttgattg cggcgcgcgc attcttgggg tttggcgcgg caacgttgat gccggctacg       420
ttagcgttga tccgcacaac attccgcgat ccgcgccagt ggctacggc gattgggatt        480 tgggcggcaa catctacgct gggcgctgcg gccggtccgg ttattggcgg cttttttgctg      540 gagcatttttt ggtggggttc gatctttttg atcaatattc cgattgcggt tggcgcgttt      600
gttgccacgt tgatgatcgc cccgccgaat gaggcgaatc cggcaaagca ttgggatgtt       660
gtttctagcg tgtatgcgat gcttgccatg ttgggcatgg tgatgtttat taaggagatt       720
tcgagctacc agaatctgtg ggttgtgtgt ggttcgttgg cggctgccgt gtgtggcggg       780
gtggcgttca aattacgcca ggataagttg cgtgagccgc ttttggagtt tgatattttc       840
cgttcgtgga tgtttacggc gggcgtgatt gctgccggca tgacgttgtt tattattggc       900
ggcgccgagt tgatgactac ccaacgtttc cagctttctg ttggtttcac gccgttacag       960
gcaggtatgt tggtggcggt tgcggcgatt tcgtccttct tcatgtctgc gattggcggc      1020
gcgattgttc atattgttgg gttccgtacg ttgattcgg gcggcttat cacgtccaca       1080 gttggcttga gtgccatgta cgttggggtt gcgaaccatg cgttgtgggt gacgatcacc      1140
```

```
ggtttggctt tcactggcgc cggggttggt ttggtgatga gcgtatcgtc tacggcgatt    1200
attggttcgg cgccgcggag ccgcgccggg atggcggccg ccgttgaaga ggtgtcgtat    1260
gagttgggta cggttatttc ggtggcgatt gtgggtagtt tgctgccgtt cttttatcgt    1320
ttgaatgttc catctgagat tgggggttcg attcacgacg ctttggctca ccccacgttg    1380
tccaatgttg cgaaggctgg gtatgacgcg gcatatttgg acatgatttt attgatgatt    1440
gccgtaacga tttttgccac cgctgtgacc gcgtatgcgt tgcgtggcaa cccgaaggag    1500
actgcgtatg cgcacgagta a                                              1521
```

<210> SEQ ID NO 6
<211> LENGTH: 506
<212> TYPE: PRT
<213> ORGANISM: Arcanobacterium haemolyticum

<400> SEQUENCE: 6

```
Met Pro Asp Val Ser Ser Pro Val Ser Gly Val Val Pro Ala Pro
1               5                   10                  15

His Pro Ala Pro Ser Ser Ala Met Ser Ala Arg Arg Lys Trp Leu Phe
                20                  25                  30

Leu Gly Val Leu Ser Ser Gly Leu Phe Leu Val Gly Val Asp Asn Ser
            35                  40                  45

Val Leu Tyr Thr Ala Leu Pro Glu Leu Arg Arg Val Leu His Thr Thr
 50                  55                  60

Glu Leu Gln Gly Leu Trp Ile Ile Asn Ala Tyr Pro Leu Val Leu Ala
65                  70                  75                  80

Gly Leu Leu Leu Gly Thr Gly Thr Leu Gly Asp Lys Ile Gly His Arg
                85                  90                  95

Arg Met Trp Met Ile Gly Leu Val Val Phe Met Phe Ala Ser Leu Gly
                100                 105                 110

Ala Ala Phe Ala Pro Gly Pro Trp Trp Leu Ile Ala Ala Arg Ala Phe
            115                 120                 125

Leu Gly Phe Gly Ala Ala Thr Leu Met Pro Ala Thr Leu Ala Leu Ile
    130                 135                 140

Arg Thr Thr Phe Arg Asp Pro Arg Gln Leu Ala Thr Ala Ile Gly Ile
145                 150                 155                 160

Trp Ala Ala Thr Ser Thr Leu Gly Ala Ala Gly Pro Val Ile Gly
                165                 170                 175

Gly Phe Leu Leu Glu His Phe Trp Trp Gly Ser Ile Phe Leu Ile Asn
                180                 185                 190

Ile Pro Ile Ala Val Gly Ala Phe Val Ala Thr Leu Met Ile Ala Pro
            195                 200                 205

Pro Asn Glu Ala Asn Pro Ala Lys His Trp Asp Val Val Ser Ser Val
    210                 215                 220

Tyr Ala Met Leu Ala Met Leu Gly Met Val Met Phe Ile Lys Glu Ile
225                 230                 235                 240

Ser Ser Tyr Gln Asn Leu Trp Val Val Cys Gly Ser Leu Ala Ala Ala
                245                 250                 255

Val Cys Gly Gly Val Ala Phe Lys Leu Arg Gln Asp Lys Leu Arg Glu
            260                 265                 270

Pro Leu Leu Glu Phe Asp Ile Phe Arg Ser Trp Met Phe Thr Ala Gly
    275                 280                 285

Val Ile Ala Ala Gly Met Thr Leu Phe Ile Ile Gly Gly Ala Glu Leu
    290                 295                 300
```

```
Met Thr Thr Gln Arg Phe Gln Leu Ser Val Gly Phe Thr Pro Leu Gln
305                 310                 315                 320

Ala Gly Met Leu Val Ala Val Ala Ala Ile Ser Ser Phe Phe Met Ser
            325                 330                 335

Ala Ile Gly Gly Ala Ile Val His Ile Val Gly Phe Arg Thr Leu Ile
                340                 345                 350

Ser Gly Gly Leu Ile Thr Ser Thr Val Gly Leu Ser Ala Met Tyr Val
        355                 360                 365

Gly Val Ala Asn His Ala Leu Trp Val Thr Ile Thr Gly Leu Ala Phe
    370                 375                 380

Thr Gly Ala Gly Val Gly Leu Val Met Ser Val Ser Ser Thr Ala Ile
385                 390                 395                 400

Ile Gly Ser Ala Pro Arg Ser Arg Ala Gly Met Ala Ala Ala Val Glu
                405                 410                 415

Glu Val Ser Tyr Glu Leu Gly Thr Val Ile Ser Val Ala Ile Val Gly
            420                 425                 430

Ser Leu Leu Pro Phe Phe Tyr Arg Leu Asn Val Pro Ser Glu Ile Gly
        435                 440                 445

Gly Ser Ile His Asp Ala Leu Ala His Pro Thr Leu Ser Asn Val Ala
    450                 455                 460

Lys Ala Gly Tyr Asp Ala Ala Tyr Leu Asp Met Ile Leu Leu Met Ile
465                 470                 475                 480

Ala Val Thr Ile Phe Ala Thr Ala Val Thr Ala Tyr Ala Leu Arg Gly
                485                 490                 495

Asn Pro Lys Glu Thr Ala Tyr Ala His Glu
            500                 505
```

<210> SEQ ID NO 7
<211> LENGTH: 1521
<212> TYPE: DNA
<213> ORGANISM: Artificial Sequence
<220> FEATURE:
<223> OTHER INFORMATION: ARCH_0271 (Codon optimized sequence)

<400> SEQUENCE: 7

```
atgccagacg tgtcctcctc ccctgtgtct ggagtggtgc cagcaccaca cccagcacca    60
tcatcggcaa tgtccgcacg ccgcaaatgg cttttcctgg gtgtgctttc ctctggtctg   120
tttctagttg gagtcgataa ctccgtgctg tataccgcac ttccagagct tcgacgtgta   180
ctccacacta ccgagttaca gggcttgtgg atcatcaacg cgtaccccact cgtgctggca   240 ggcctgctgc tgggcactgg taccctgggc gacaaaatcg ccaccgccg tatgtggatg   300 atcggcttgg ttgtgttcat gttcgcgagc ctgggagccg cttttgcacc aggcccatgg   360
tggctgattg ccgcacgcgc atttcttgga ttcggcgcag ctaccctgat gccagctacc   420
ttagcattga tccgaactac ctttcgcgat cctcgccagc tggcaacagc aattggcata   480
tgggctgcaa cctccaccct ggcgcagca gccggcccag ttatcggtgg cttcctgttg   540
gaacacttct ggtgggggtc tattttccta atcaacattc caatcgcagt gggagcgttc   600
gtggcaaccc tgatgatcgc accaccaaac gaggcaaacc cagcaaagca ctgggatgta   660
gtgtcctccg tttatgcaat gctggcaatg cttggaatgg tgatgttcat caaggaaatc   720
tcctcatatc aaaacctgtg gtggtgtgc ggctccttgg cagcagcagt atgtggaggc   780
gttgcattca aactgcgtca agataagctt agggaacctt tgctggaatt cgacattttc   840
cgcagttgga tgtttaccgc tggcgttatt gcagcaggaa tgaccctatt catcatcgga   900
```

```
ggcgcagaac tgatgaccac tcaacgcttt cagctgtccg tggggtttac cccattgcag    960
gctggcatgt tggtggctgt tgcagcaatt agctcgtttt tcatgtccgc aatcggcggc   1020
gcaattgtgc atatcgttgg atttcggacg ctgatctcag gcggcctgat cacatccact   1080
gtgggcctat ccgcaatgta cgtgggcgtt gcaaatcatg cactgtgggt gaccatcacc   1140
ggattagcgt ttaccggtgc tggtgtagga ctggttatgt ctgtgtctag tacggccatc   1200
atcggttcgg cacctcgttc ccgcgcaggg atggcagcag cagtggaaga agtatcctac   1260
gagctgggca ccgtgatctc agtggcaatc gtgggtagcc tgcttccatt cttctaccgc   1320
ctcaatgtcc catccgagat cggcggttcc attcatgatg cactggcaca cccaaccctg   1380
tcgaacgtcg caaaggcagg gtacgatgca gcataccttg acatgatttt gctgatgatc   1440
gcagtgacca tcttcgcaac tgcagtgacc gcttacgccc tgcgtggtaa tccaaaggag   1500
acagcatatg cacacgaata a                                             1521
```

<210> SEQ ID NO 8
<211> LENGTH: 40
<212> TYPE: DNA
<213> ORGANISM: Artificial Sequence
<220> FEATURE:
<223> OTHER INFORMATION: CJ7-F Primer

<400> SEQUENCE: 8
tgtcgggccc actagtagaa acatcccagc gctactaata    40

<210> SEQ ID NO 9
<211> LENGTH: 23
<212> TYPE: DNA
<213> ORGANISM: Artificial Sequence
<220> FEATURE:
<223> OTHER INFORMATION: CJ7-R Primer

<400> SEQUENCE: 9
agtgtttcct ttcgttgggt acg    23

<210> SEQ ID NO 10
<211> LENGTH: 35
<212> TYPE: DNA
<213> ORGANISM: Artificial Sequence
<220> FEATURE:
<223> OTHER INFORMATION: ARCH_0271-F Primer

<400> SEQUENCE: 10
caacgaaagg aaacactatg ccagacgtgt cctcc    35

<210> SEQ ID NO 11
<211> LENGTH: 34
<212> TYPE: DNA
<213> ORGANISM: Artificial Sequence
<220> FEATURE:
<223> OTHER INFORMATION: ARCH_0271-R Primer

<400> SEQUENCE: 11
gaatgagttc ctcgagttat tcgtgtgcat atgc    34

<210> SEQ ID NO 12
<211> LENGTH: 203
<212> TYPE: PRT
<213> ORGANISM: Corynebacterium glutamicum
<220> FEATURE:
<221> NAME/KEY: MISC_FEATURE
<222> LOCATION: (1)..(203)
<223> OTHER INFORMATION: NCgl1469

<400> SEQUENCE: 12

Met Ser Pro Thr Val Leu Pro Ala Thr Gln Ala Asp Phe Pro Lys Ile
1               5                   10                  15

Val Asp Val Leu Val Glu Ala Phe Ala Asn Asp Pro Ala Phe Leu Arg
            20                  25                  30

Trp Ile Pro Gln Pro Asp Pro Gly Ser Ala Lys Leu Arg Ala Leu Phe
        35                  40                  45

Glu Leu Gln Ile Glu Lys Gln Tyr Ala Val Ala Gly Asn Ile Asp Val
    50                  55                  60

Ala Arg Asp Ser Glu Gly Glu Ile Val Gly Val Ala Leu Trp Asp Arg
65                  70                  75                  80

Pro Asp Gly Asn His Ser Ala Lys Asp Gln Ala Ala Met Leu Pro Arg
                85                  90                  95

Leu Val Ser Ile Phe Gly Ile Lys Ala Ala Gln Val Ala Trp Thr Asp
            100                 105                 110

Leu Ser Ser Ala Arg Phe His Pro Lys Phe Pro His Trp Tyr Leu Tyr
        115                 120                 125

Thr Val Ala Thr Ser Ser Ser Ala Arg Gly Thr Gly Val Gly Ser Ala
130                 135                 140

Leu Leu Asn His Gly Ile Ala Arg Ala Gly Asp Glu Ala Ile Tyr Leu
145                 150                 155                 160

Glu Ala Thr Ser Thr Arg Ala Ala Gln Leu Tyr Asn Arg Leu Gly Phe
                165                 170                 175

Val Pro Leu Gly Tyr Ile Pro Ser Asp Asp Gly Thr Pro Glu Leu
            180                 185                 190

Ala Met Trp Lys Pro Pro Ala Met Pro Thr Val
        195                 200

<210> SEQ ID NO 13
<211> LENGTH: 203
<212> TYPE: PRT
<213> ORGANISM: Corynebacterium glutamicum
<220> FEATURE:
<221> NAME/KEY: MISC_FEATURE
<222> LOCATION: (1)..(203)
<223> OTHER INFORMATION: NCgl1469

<400> SEQUENCE: 13

Met Ser Pro Thr Val Leu Pro Ala Thr Gln Ala Asp Phe Pro Lys Ile
1               5                   10                  15

Val Asp Val Leu Val Glu Ala Phe Ala Asn Asp Pro Ala Phe Leu Arg
            20                  25                  30

Trp Ile Pro Gln Pro Asp Pro Gly Ser Ala Lys Leu Arg Ala Leu Phe
        35                  40                  45

Glu Leu Gln Ile Glu Lys Gln Tyr Ala Val Ala Gly Asn Ile Asp Val
    50                  55                  60

Ala Arg Asp Ser Glu Gly Glu Ile Val Gly Val Ala Leu Trp Asp Arg
65                  70                  75                  80

Pro Asp Gly Asn His Ser Ala Lys Asp Gln Ala Ala Ile Leu Pro Arg
                85                  90                  95

Leu Val Ser Ile Phe Gly Ile Lys Ala Ala Gln Val Ala Trp Thr Asp
            100                 105                 110

Leu Ser Ser Ala Arg Phe His Pro Lys Phe Pro His Trp Tyr Leu Tyr
        115                 120                 125

Thr Val Ala Thr Ser Ser Ser Ala Arg Gly Thr Gly Val Gly Ser Ala

```
                130               135               140
Leu Leu Asn His Gly Ile Ala Arg Ala Gly Asp Glu Ala Ile Tyr Leu
145                 150                 155                 160

Glu Ala Thr Ser Thr Arg Ala Ala Gln Leu Tyr Asn Arg Leu Gly Phe
                165                 170                 175

Val Pro Leu Gly Tyr Ile Pro Ser Asp Asp Gly Thr Pro Glu Leu
            180                 185                 190

Ala Met Trp Lys Pro Pro Ala Met Pro Thr Val
            195                 200
```

```
<210> SEQ ID NO 14
<211> LENGTH: 186
<212> TYPE: PRT
<213> ORGANISM: Escherichia Coli
<220> FEATURE:
<221> NAME/KEY: MISC_FEATURE
<222> LOCATION: (1)..(186)
<223> OTHER INFORMATION: SpeG (E.coli) W3110

<400> SEQUENCE: 14

Met Pro Ser Ala His Ser Val Lys Leu Arg Pro Leu Glu Arg Glu Asp
1               5                   10                  15

Leu Arg Tyr Val His Gln Leu Asp Asn Ala Ser Val Met Arg Tyr
                20                  25                  30

Trp Phe Glu Glu Pro Tyr Glu Ala Phe Val Glu Leu Ser Asp Leu Tyr
            35                  40                  45

Asp Lys His Ile His Asp Gln Ser Glu Arg Arg Phe Val Val Glu Cys
50                  55                  60

Asp Gly Glu Lys Ala Gly Leu Val Glu Leu Val Glu Ile Asn His Val
65                  70                  75                  80

His Arg Arg Ala Glu Phe Gln Ile Ile Ile Ser Pro Glu Tyr Gln Gly
                85                  90                  95

Lys Gly Leu Ala Thr Arg Ala Ala Lys Leu Ala Met Asp Tyr Gly Phe
            100                 105                 110

Thr Val Leu Asn Leu Tyr Lys Leu Tyr Leu Ile Val Asp Lys Glu Asn
                115                 120                 125

Glu Lys Ala Ile His Ile Tyr Arg Lys Leu Gly Phe Ser Val Glu Gly
            130                 135                 140

Glu Leu Met His Glu Phe Phe Ile Asn Gly Gln Tyr Arg Asn Ala Ile
145                 150                 155                 160

Arg Met Cys Ile Phe Gln His Gln Tyr Leu Ala Glu His Lys Thr Pro
                165                 170                 175

Gly Gln Thr Leu Leu Lys Pro Thr Ala Gln
            180                 185
```

```
<210> SEQ ID NO 15
<211> LENGTH: 357
<212> TYPE: PRT
<213> ORGANISM: Corynebacterium glutamicum
<220> FEATURE:
<221> NAME/KEY: MISC_FEATURE
<222> LOCATION: (1)..(357)
<223> OTHER INFORMATION: Acetyl gamma glutamyl phosphate reductase
      (ArgC)

<400> SEQUENCE: 15

Met Ile Met His Asn Val Tyr Gly Val Thr Met Thr Ile Lys Val Ala
1               5                   10                  15

Ile Ala Gly Ala Ser Gly Tyr Ala Gly Gly Glu Ile Leu Arg Leu Leu
```

```
            20                  25                  30
Leu Gly His Pro Ala Tyr Ala Ser Gly Glu Leu Glu Ile Gly Ala Leu
        35                  40                  45

Thr Ala Ala Ser Thr Ala Gly Ser Thr Leu Gly Glu Leu Met Pro His
    50                  55                  60

Ile Pro Gln Leu Ala Asp Arg Val Ile Gln Asp Thr Thr Ala Glu Thr
65                  70                  75                  80

Leu Ala Gly His Asp Val Val Phe Leu Gly Leu Pro His Gly Phe Ser
                85                  90                  95

Ala Glu Ile Ala Leu Gln Leu Gly Pro Asp Val Thr Val Ile Asp Cys
            100                 105                 110

Ala Ala Asp Phe Arg Leu Gln Asn Ala Ala Asp Trp Glu Lys Phe Tyr
        115                 120                 125

Gly Ser Glu His Gln Gly Thr Trp Pro Tyr Gly Ile Pro Glu Met Pro
    130                 135                 140

Gly His Arg Glu Ala Leu Arg Gly Ala Lys Arg Val Ala Val Pro Gly
145                 150                 155                 160

Cys Phe Pro Thr Gly Ala Thr Leu Ala Leu Leu Pro Ala Val Gln Ala
                165                 170                 175

Gly Leu Ile Glu Pro Asp Val Ser Val Ser Ile Thr Gly Val Ser
            180                 185                 190

Gly Ala Gly Lys Lys Ala Ser Val Ala Leu Leu Gly Ser Glu Thr Met
        195                 200                 205

Gly Ser Leu Lys Ala Tyr Asn Thr Ser Gly Lys His Arg His Thr Pro
    210                 215                 220

Glu Ile Ala Gln Asn Leu Gly Glu Val Ser Asp Lys Pro Val Lys Val
225                 230                 235                 240

Ser Phe Thr Pro Val Leu Ala Pro Leu Pro Arg Gly Ile Leu Thr Thr
                245                 250                 255

Ala Thr Ala Pro Leu Lys Glu Gly Val Thr Ala Glu Gln Ala Arg Ala
            260                 265                 270

Val Tyr Glu Glu Phe Tyr Ala Gln Glu Thr Phe Val His Val Leu Pro
        275                 280                 285

Glu Gly Ala Gln Pro Gln Thr Gln Ala Val Leu Gly Ser Asn Met Cys
    290                 295                 300

His Val Gln Val Glu Ile Asp Glu Glu Ala Gly Lys Val Leu Val Thr
305                 310                 315                 320

Ser Ala Ile Asp Asn Leu Thr Lys Gly Thr Ala Gly Ala Ala Val Gln
                325                 330                 335

Cys Met Asn Leu Ser Val Gly Phe Asp Glu Ala Ala Gly Leu Pro Gln
            340                 345                 350

Val Gly Val Ala Pro
        355

<210> SEQ ID NO 16
<211> LENGTH: 388
<212> TYPE: PRT
<213> ORGANISM: Corynebacterium glutamicum
<220> FEATURE:
<221> NAME/KEY: MISC_FEATURE
<222> LOCATION: (1)..(388)
<223> OTHER INFORMATION: Acetyl glutamate synthase or Ornithine acetyl
      transferase (ArgJ)

<400> SEQUENCE: 16

Met Ala Glu Lys Gly Ile Thr Ala Pro Lys Gly Phe Val Ala Ser Ala
1               5                   10                  15
```

Thr Thr Ala Gly Ile Lys Ala Ser Gly Asn Pro Asp Met Ala Leu Val
            20                  25                  30

Val Asn Gln Gly Pro Glu Phe Ser Ala Ala Val Phe Thr Arg Asn
        35                  40                  45

Arg Val Phe Ala Ala Pro Val Lys Val Ser Arg Glu Asn Val Ala Asp
 50                  55                  60

Gly Gln Ile Arg Ala Val Leu Tyr Asn Ala Gly Asn Ala Asn Ala Cys
 65                  70                  75                  80

Asn Gly Leu Gln Gly Glu Lys Asp Ala Arg Glu Ser Val Ser His Leu
                85                  90                  95

Ala Gln Asn Leu Gly Leu Glu Asp Ser Asp Ile Gly Val Cys Ser Thr
            100                 105                 110

Gly Leu Ile Gly Glu Leu Leu Pro Met Asp Lys Leu Asn Ala Gly Ile
            115                 120                 125

Asp Gln Leu Thr Ala Glu Gly Ala Leu Gly Asp Asn Gly Ala Ala Ala
130                 135                 140

Ala Lys Ala Ile Met Thr Thr Asp Thr Val Asp Lys Glu Thr Val Val
145                 150                 155                 160

Phe Ala Asp Gly Trp Thr Val Gly Gly Met Gly Lys Gly Val Gly Met
                165                 170                 175

Met Ala Pro Ser Leu Ala Thr Met Leu Val Cys Leu Thr Thr Asp Ala
            180                 185                 190

Ser Val Thr Gln Glu Met Ala Gln Ile Ala Leu Ala Asn Ala Thr Ala
            195                 200                 205

Val Thr Phe Asp Thr Leu Asp Ile Asp Gly Ser Thr Ser Thr Asn Asp
        210                 215                 220

Thr Val Phe Leu Leu Ala Ser Gly Ala Ser Gly Ile Thr Pro Thr Gln
225                 230                 235                 240

Asp Glu Leu Asn Asp Ala Val Tyr Ala Ala Cys Ser Asp Ile Ala Ala
                245                 250                 255

Lys Leu Gln Ala Asp Ala Glu Gly Val Thr Lys Arg Val Ala Val Thr
            260                 265                 270

Val Val Gly Thr Thr Asn Asn Glu Gln Ala Ile Asn Ala Ala Arg Thr
            275                 280                 285

Val Ala Arg Asp Asn Leu Phe Lys Cys Ala Met Phe Gly Ser Asp Pro
290                 295                 300

Asn Trp Gly Arg Val Leu Ala Ala Val Gly Met Ala Asp Ala Asp Met
305                 310                 315                 320

Glu Pro Glu Lys Ile Ser Val Phe Phe Asn Gly Gln Ala Val Cys Leu
                325                 330                 335

Asp Ser Thr Gly Ala Pro Gly Ala Arg Glu Val Asp Leu Ser Gly Ala
            340                 345                 350

Asp Ile Asp Val Arg Ile Asp Leu Gly Thr Ser Gly Glu Gly Gln Ala
            355                 360                 365

Thr Val Arg Thr Thr Asp Leu Ser Phe Ser Tyr Val Glu Ile Asn Ser
            370                 375                 380

Ala Tyr Ser Ser
385

<210> SEQ ID NO 17
<211> LENGTH: 317
<212> TYPE: PRT
<213> ORGANISM: Corynebacterium sp.
<220> FEATURE:

<221> NAME/KEY: MISC_FEATURE
<222> LOCATION: (1)..(317)
<223> OTHER INFORMATION: Acetyl glutamate kinase (ArgB)

<400> SEQUENCE: 17

Met Asn Asp Leu Ile Lys Asp Leu Gly Ser Glu Val Arg Ala Asn Val
1               5                   10                  15

Leu Ala Glu Ala Leu Pro Trp Leu Gln His Phe Arg Asp Lys Ile Val
            20                  25                  30

Val Val Lys Tyr Gly Gly Asn Ala Met Val Asp Asp Leu Lys Ala
        35                  40                  45

Ala Phe Ala Ala Asp Met Val Phe Leu Arg Thr Val Gly Ala Lys Pro
    50                  55                  60

Val Val His Gly Gly Gly Pro Gln Ile Ser Glu Met Leu Asn Arg
65                  70                  75                  80

Val Gly Leu Gln Gly Glu Phe Lys Gly Phe Arg Val Thr Thr Pro
            85                  90                  95

Glu Val Met Asp Ile Val Arg Met Val Leu Phe Gly Gln Val Gly Arg
            100                 105                 110

Asp Leu Val Gly Leu Ile Asn Ser His Gly Pro Tyr Ala Val Gly Thr
            115                 120                 125

Ser Gly Glu Asp Ala Gly Leu Phe Thr Ala Gln Lys Arg Met Val Asn
    130                 135                 140

Ile Asp Gly Val Pro Thr Asp Ile Gly Leu Val Gly Asp Ile Ile Asn
145                 150                 155                 160

Val Asp Ala Ser Ser Leu Met Asp Ile Ile Glu Ala Gly Arg Ile Pro
                165                 170                 175

Val Val Ser Thr Ile Ala Pro Gly Glu Asp Gly Gln Ile Tyr Asn Ile
            180                 185                 190

Asn Ala Asp Thr Ala Ala Gly Ala Leu Ala Ala Ile Gly Ala Glu
    195                 200                 205

Arg Leu Leu Val Leu Thr Asn Val Glu Gly Leu Tyr Thr Asp Trp Pro
        210                 215                 220

Asp Lys Ser Ser Leu Val Ser Lys Ile Lys Ala Thr Glu Leu Glu Ala
225                 230                 235                 240

Ile Leu Pro Gly Leu Asp Ser Gly Met Ile Pro Lys Met Glu Ser Cys
                245                 250                 255

Leu Asn Ala Val Arg Gly Gly Val Ser Ala Ala His Val Ile Asp Gly
            260                 265                 270

Arg Ile Ala His Ser Val Leu Leu Glu Leu Leu Thr Met Gly Gly Ile
        275                 280                 285

Gly Thr Met Val Leu Pro Asp Val Phe Asp Arg Glu Asn Tyr Pro Glu
    290                 295                 300

Gly Thr Val Phe Arg Lys Asp Lys Asp Gly Glu Leu
305                 310                 315

<210> SEQ ID NO 18
<211> LENGTH: 391
<212> TYPE: PRT
<213> ORGANISM: Corynebacterium glutamicum
<220> FEATURE:
<221> NAME/KEY: MISC_FEATURE
<222> LOCATION: (1)..(391)
<223> OTHER INFORMATION: Acetyl ornithine aminotransferase (ArgD)

<400> SEQUENCE: 18

Met Ser Thr Leu Glu Thr Trp Pro Gln Val Ile Ile Asn Thr Tyr Gly

```
            1               5                  10                 15
          Thr Pro Pro Val Glu Leu Val Ser Gly Lys Gly Ala Thr Val Thr Asp
                          20                 25                 30

Asp Gln Gly Asn Val Tyr Ile Asp Leu Leu Ala Gly Ile Ala Val Asn
                          35                 40                 45

Ala Leu Gly His Ala His Pro Ala Ile Ile Glu Ala Val Thr Asn Gln
           50                  55                 60

Ile Gly Gln Leu Gly His Val Ser Asn Leu Phe Ala Ser Arg Pro Val
           65                  70                 75                 80

Val Glu Val Ala Glu Glu Leu Ile Lys Arg Phe Ser Leu Asp Asp Ala
                          85                 90                 95

Thr Leu Ala Ala Gln Thr Arg Val Phe Phe Cys Asn Ser Gly Ala Glu
                          100                105                110

Ala Asn Glu Ala Ala Phe Lys Ile Ala Arg Leu Thr Gly Arg Ser Arg
                          115                120                125

Ile Leu Ala Ala Val His Gly Phe His Gly Arg Thr Met Gly Ser Leu
           130                 135                140

Ala Leu Thr Gly Gln Pro Asp Lys Arg Glu Ala Phe Leu Pro Met Pro
          145                 150                155                160

Ser Gly Val Glu Phe Tyr Pro Tyr Gly Asp Thr Asp Tyr Leu Arg Lys
                          165                170                175

Met Val Glu Thr Asn Pro Thr Asp Val Ala Ala Ile Phe Leu Glu Pro
                          180                185                190

Ile Gln Gly Glu Thr Gly Val Val Pro Ala Pro Glu Gly Phe Leu Lys
                          195                200                205

Ala Val Arg Glu Leu Cys Asp Glu Tyr Gly Ile Leu Met Ile Thr Asp
           210                 215                220

Glu Val Gln Thr Gly Val Gly Arg Thr Gly Asp Phe Phe Ala His Gln
          225                 230                235                240

His Asp Gly Val Val Pro Asp Val Val Thr Met Ala Lys Gly Leu Gly
                          245                250                255

Gly Gly Leu Pro Ile Gly Ala Cys Leu Ala Thr Gly Arg Ala Ala Glu
                          260                265                270

Leu Met Thr Pro Gly Lys His Gly Thr Thr Phe Gly Gly Asn Pro Val
                          275                280                285

Ala Cys Ala Ala Ala Lys Ala Val Leu Ser Val Val Asp Asp Ala Phe
                          290                295                300

Cys Ala Glu Val Ala Arg Lys Gly Glu Leu Phe Lys Glu Leu Leu Ala
          305                 310                315                320

Lys Val Asp Gly Val Val Asp Val Arg Gly Arg Gly Leu Met Leu Gly
                          325                330                335

Val Val Leu Glu Arg Asp Val Ala Lys Gln Ala Val Leu Asp Gly Phe
                          340                345                350

Lys His Gly Val Ile Leu Asn Ala Pro Ala Asp Asn Ile Ile Arg Leu
                          355                360                365

Thr Pro Pro Leu Val Ile Thr Asp Glu Glu Ile Ala Asp Ala Val Lys
                          370                375                380

Ala Ile Ala Glu Thr Ile Ala
          385                 390

<210> SEQ ID NO 19
<211> LENGTH: 319
<212> TYPE: PRT
<213> ORGANISM: Corynebacterium glutamicum
```

<220> FEATURE:
<221> NAME/KEY: MISC_FEATURE
<222> LOCATION: (1)..(319)
<223> OTHER INFORMATION: Ornithine carbamoyl transferase (argF)

<400> SEQUENCE: 19

| | | | | | | | | | | | | | | |
|---|---|---|---|---|---|---|---|---|---|---|---|---|---|---|
| Met | Thr | Ser | Gln | Pro | Gln | Val | Arg | His | Phe | Leu | Ala | Asp | Asp | Leu |
| 1 | | | | 5 | | | | | 10 | | | | | 15 |
| Thr | Pro | Ala | Glu | Gln | Ala | Glu | Val | Leu | Thr | Leu | Ala | Ala | Lys | Leu | Lys |
| | | | 20 | | | | | 25 | | | | | 30 | | |
| Ala | Ala | Pro | Phe | Ser | Glu | Arg | Pro | Leu | Glu | Gly | Pro | Lys | Ser | Val | Ala |
| | | | 35 | | | | | 40 | | | | | 45 | | |
| Val | Leu | Phe | Asp | Lys | Thr | Ser | Thr | Arg | Thr | Arg | Phe | Ser | Phe | Asp | Ala |
| | 50 | | | | | 55 | | | | | 60 | | | | |
| Gly | Ile | Ala | His | Leu | Gly | Gly | His | Ala | Ile | Val | Val | Asp | Ser | Gly | Ser |
| 65 | | | | | 70 | | | | | 75 | | | | | 80 |
| Ser | Gln | Met | Gly | Lys | Gly | Glu | Ser | Leu | Gln | Asp | Thr | Ala | Ala | Val | Leu |
| | | | | 85 | | | | | 90 | | | | | 95 | |
| Ser | Arg | Tyr | Val | Glu | Ala | Ile | Val | Trp | Arg | Thr | Tyr | Ala | His | Ser | Asn |
| | | | 100 | | | | | 105 | | | | | 110 | | |
| Phe | His | Ala | Met | Ala | Glu | Thr | Ser | Thr | Val | Pro | Leu | Val | Asn | Ser | Leu |
| | | | 115 | | | | | 120 | | | | | 125 | | |
| Ser | Asp | Asp | Leu | His | Pro | Cys | Gln | Ile | Leu | Ala | Asp | Leu | Gln | Thr | Ile |
| | 130 | | | | | 135 | | | | | 140 | | | | |
| Val | Glu | Asn | Leu | Ser | Pro | Glu | Glu | Gly | Pro | Ala | Gly | Leu | Lys | Gly | Lys |
| 145 | | | | | 150 | | | | | 155 | | | | | 160 |
| Lys | Ala | Val | Tyr | Leu | Gly | Asp | Gly | Asp | Asn | Asn | Met | Ala | Asn | Ser | Tyr |
| | | | | 165 | | | | | 170 | | | | | 175 | |
| Met | Ile | Gly | Phe | Ala | Thr | Ala | Gly | Met | Asp | Ile | Ser | Ile | Ile | Ala | Pro |
| | | | 180 | | | | | 185 | | | | | 190 | | |
| Glu | Gly | Phe | Gln | Pro | Arg | Ala | Glu | Phe | Val | Glu | Arg | Ala | Glu | Lys | Arg |
| | | | 195 | | | | | 200 | | | | | 205 | | |
| Gly | Gln | Glu | Thr | Gly | Ala | Lys | Val | Val | Val | Thr | Asp | Ser | Leu | Asp | Glu |
| | 210 | | | | | 215 | | | | | 220 | | | | |
| Val | Ala | Gly | Ala | Asp | Val | Val | Ile | Thr | Asp | Thr | Trp | Val | Ser | Met | Gly |
| 225 | | | | | 230 | | | | | 235 | | | | | 240 |
| Met | Glu | Asn | Asp | Gly | Ile | Asp | Arg | Thr | Thr | Pro | Phe | Val | Pro | Tyr | Gln |
| | | | | 245 | | | | | 250 | | | | | 255 | |
| Val | Asn | Asp | Glu | Val | Met | Ala | Lys | Ala | Asn | Asp | Gly | Ala | Ile | Phe | Leu |
| | | | 260 | | | | | 265 | | | | | 270 | | |
| His | Cys | Leu | Pro | Ala | Tyr | Arg | Gly | Lys | Glu | Val | Ala | Ala | Ser | Val | Ile |
| | | | 275 | | | | | 280 | | | | | 285 | | |
| Asp | Gly | Pro | Ala | Ser | Lys | Val | Phe | Asp | Glu | Ala | Glu | Asn | Arg | Leu | His |
| | 290 | | | | | 295 | | | | | 300 | | | | |
| Ala | Gln | Lys | Ala | Leu | Leu | Val | Trp | Leu | Leu | Ala | Asn | Gln | Pro | Arg |
| 305 | | | | | 310 | | | | | 315 | | | | | |

<210> SEQ ID NO 20
<211> LENGTH: 533
<212> TYPE: PRT
<213> ORGANISM: Corynebacterium glutamicum
<220> FEATURE:
<221> NAME/KEY: MISC_FEATURE
<222> LOCATION: (1)..(533)
<223> OTHER INFORMATION: Glutamate expoter (NCgl1221)

<400> SEQUENCE: 20

```
Met Ile Leu Gly Val Pro Ile Gln Tyr Leu Tyr Ser Leu Trp Asn
1               5                   10                  15

Trp Ile Val Asp Thr Gly Phe Asp Val Ala Ile Ile Leu Val Leu Ala
                20                  25                  30

Phe Leu Ile Pro Arg Ile Gly Arg Leu Ala Met Arg Ile Ile Lys Arg
            35                  40                  45

Arg Val Glu Ser Ala Ala Asp Ala Asp Thr Thr Lys Asn Gln Leu Ala
        50                  55                  60

Phe Ala Gly Val Gly Val Tyr Ile Ala Gln Ile Val Ala Phe Phe Met
65                  70                  75                  80

Leu Ala Val Ser Ala Met Gln Ala Phe Gly Phe Ser Leu Ala Gly Ala
                85                  90                  95

Ala Ile Pro Ala Thr Ile Ala Ser Ala Ala Ile Gly Leu Gly Ala Gln
            100                 105                 110

Ser Ile Val Ala Asp Phe Leu Ala Gly Phe Phe Ile Leu Thr Glu Lys
        115                 120                 125

Gln Phe Gly Val Gly Asp Trp Val Arg Phe Glu Gly Asn Gly Ile Val
    130                 135                 140

Val Glu Gly Thr Val Ile Glu Ile Thr Met Arg Ala Thr Lys Ile Arg
145                 150                 155                 160

Thr Ile Ala Gln Glu Thr Val Ile Ile Pro Asn Ser Thr Ala Lys Val
                165                 170                 175

Cys Ile Asn Asn Ser Asn Asn Trp Ser Arg Ala Val Val Ile Pro
            180                 185                 190

Ile Pro Met Leu Gly Ser Glu Asn Ile Thr Asp Val Ile Ala Arg Ser
        195                 200                 205

Glu Ala Ala Thr Arg Arg Ala Leu Gly Gln Glu Lys Ile Ala Pro Glu
    210                 215                 220

Ile Leu Gly Glu Leu Asp Val His Pro Ala Thr Glu Val Thr Pro Pro
225                 230                 235                 240

Thr Val Val Gly Met Pro Trp Met Val Thr Met Arg Phe Leu Val Gln
                245                 250                 255

Val Thr Ala Gly Asn Gln Trp Leu Val Glu Arg Ala Ile Arg Thr Glu
            260                 265                 270

Ile Ile Ser Glu Phe Trp Glu Glu Tyr Gly Ser Ala Thr Thr Thr Ser
        275                 280                 285

Gly Thr Leu Ile Asp Ser Leu His Val Glu His Glu Glu Pro Lys Thr
    290                 295                 300

Ser Leu Ile Asp Ala Ser Pro Gln Ala Leu Lys Glu Pro Lys Pro Glu
305                 310                 315                 320

Ala Ala Ala Thr Val Ala Ser Leu Ala Ala Ser Ser Asn Asp Ala
                325                 330                 335

Asp Asn Ala Asp Ala Ser Val Ile Asn Ala Gly Asn Pro Glu Lys Glu
            340                 345                 350

Leu Asp Ser Asp Val Leu Glu Gln Glu Leu Ser Glu Glu Pro Glu
        355                 360                 365

Glu Thr Ala Lys Pro Asp His Ser Leu Arg Gly Phe Phe Arg Thr Asp
    370                 375                 380

Tyr Tyr Pro Asn Arg Trp Gln Lys Ile Leu Ser Phe Gly Gly Arg Val
385                 390                 395                 400

Arg Met Ser Thr Ser Leu Leu Leu Gly Ala Leu Leu Leu Ser Leu
                405                 410                 415

Phe Lys Val Met Thr Val Glu Pro Ser Glu Asn Trp Gln Asn Ser Ser
```

```
                    420                 425                 430
Gly Trp Leu Ser Pro Ser Thr Ala Thr Ser Thr Ala Val Thr Thr Ser
                435                 440                 445
Glu Thr Ser Ala Pro Val Ser Thr Pro Ser Met Thr Val Pro Thr Thr
            450                 455                 460
Val Glu Glu Thr Pro Thr Met Glu Ser Asn Val Glu Thr Gln Gln Glu
465                 470                 475                 480
Thr Ser Thr Pro Ala Thr Ala Thr Pro Gln Arg Ala Asp Thr Ile Glu
                485                 490                 495
Pro Thr Glu Glu Ala Thr Ser Gln Gly Glu Thr Thr Ala Ser Gln Thr
                500                 505                 510
Gln Ser Pro Ala Val Glu Ala Pro Thr Ala Val Gln Glu Thr Val Ala
            515                 520                 525
Pro Thr Ser Thr Pro
            530
```

<210> SEQ ID NO 21
<211> LENGTH: 711
<212> TYPE: PRT
<213> ORGANISM: Unknown
<220> FEATURE:
<223> OTHER INFORMATION: Multispecies proteobacteria ornithine
    decarboxylase (ODC) protein sequence

<400> SEQUENCE: 21

```
Met Lys Ser Met Asn Ile Ala Ala Ser Ser Glu Leu Val Ser Arg Leu
1               5                   10                  15
Ser Ser His Arg Arg Val Val Ala Leu Gly Asp Thr Asp Phe Thr Asp
                20                  25                  30
Val Ala Val Val Ile Thr Ala Ala Asp Ser Arg Ser Gly Ile Leu
            35                  40                  45
Ala Leu Leu Lys Arg Thr Gly Phe His Leu Pro Val Phe Leu Tyr Ser
        50                  55                  60
Glu His Ala Val Glu Leu Pro Ala Gly Val Thr Ala Val Ile Asn Gly
65                  70                  75                  80
Asn Glu Gln Gln Trp Leu Glu Leu Glu Ser Ala Ala Cys Gln Tyr Glu
                85                  90                  95
Glu Asn Leu Leu Pro Pro Phe Tyr Asp Thr Leu Thr Gln Tyr Val Glu
            100                 105                 110
Met Gly Asn Ser Thr Phe Ala Cys Pro Gly His Gln His Gly Ala Phe
        115                 120                 125
Phe Lys Lys His Pro Ala Gly Arg His Phe Tyr Asp Phe Phe Gly Glu
        130                 135                 140
Asn Val Phe Arg Ala Asp Met Cys Asn Ala Asp Val Lys Leu Gly Asp
145                 150                 155                 160
Leu Leu Ile His Glu Gly Ser Ala Lys Asp Ala Gln Lys Phe Ala Ala
                165                 170                 175
Lys Val Phe His Ala Asp Lys Thr Tyr Phe Val Leu Asn Gly Thr Ser
            180                 185                 190
Ala Ala Asn Lys Val Val Thr Asn Ala Leu Leu Thr Arg Gly Asp Leu
        195                 200                 205
Val Leu Phe Asp Arg Asn Asn His Lys Ser Asn His His Gly Ala Leu
        210                 215                 220
Ile Gln Ala Gly Ala Thr Pro Val Tyr Leu Glu Ala Ser Arg Asn Pro
225                 230                 235                 240
```

-continued

Phe Gly Phe Ile Gly Gly Ile Asp Ala His Cys Phe Asn Glu Glu Tyr
            245                 250                 255

Leu Arg Gln Gln Ile Arg Asp Val Ala Pro Glu Lys Ala Asp Leu Pro
        260                 265                 270

Arg Pro Tyr Arg Leu Ala Ile Ile Gln Leu Gly Thr Tyr Asp Gly Thr
            275                 280                 285

Val Tyr Asn Ala Arg Gln Val Ile Asp Thr Val Gly His Leu Cys Asp
290                 295                 300

Tyr Ile Leu Phe Asp Ser Ala Trp Val Gly Tyr Glu Gln Phe Ile Pro
305                 310                 315                 320

Met Met Ala Asp Ser Ser Pro Leu Leu Glu Leu Asn Glu Asn Asp
                325                 330                 335

Pro Gly Ile Phe Val Thr Gln Ser Val His Lys Gln Ala Gly Phe
            340                 345                 350

Ser Gln Thr Ser Gln Ile His Lys Lys Asp Asn His Ile Arg Gly Gln
            355                 360                 365

Ala Arg Phe Cys Pro His Lys Arg Leu Asn Asn Ala Phe Met Leu His
        370                 375                 380

Ala Ser Thr Ser Pro Phe Tyr Pro Leu Phe Ala Ala Leu Asp Val Asn
385                 390                 395                 400

Ala Lys Ile His Glu Gly Glu Ser Gly Arg Arg Leu Trp Ala Glu Cys
            405                 410                 415

Val Glu Ile Gly Ile Glu Ala Arg Lys Ala Ile Leu Ala Arg Cys Lys
            420                 425                 430

Leu Phe Arg Pro Phe Ile Pro Pro Val Asp Gly Lys Leu Trp Gln
        435                 440                 445

Asp Tyr Pro Thr Ser Val Leu Ala Ser Asp Arg Arg Phe Phe Ser Phe
        450                 455                 460

Glu Pro Gly Ala Lys Trp His Gly Phe Glu Gly Tyr Ala Ala Asp Gln
465                 470                 475                 480

Tyr Phe Val Asp Pro Cys Lys Leu Leu Leu Thr Thr Pro Gly Ile Asp
            485                 490                 495

Ala Glu Thr Gly Glu Tyr Ser Asp Phe Gly Val Pro Ala Thr Ile Leu
            500                 505                 510

Ala His Tyr Leu Arg Glu Asn Gly Ile Val Pro Glu Lys Cys Asp Leu
        515                 520                 525

Asn Ser Ile Leu Phe Leu Leu Thr Pro Ala Glu Ser His Glu Lys Leu
        530                 535                 540

Ala Gln Leu Val Ala Met Leu Ala Gln Phe Glu Gln His Ile Glu Asp
545                 550                 555                 560

Asp Ser Pro Leu Val Glu Val Leu Pro Ser Val Tyr Asn Lys Tyr Pro
            565                 570                 575

Val Arg Tyr Arg Asp Tyr Thr Leu Arg Gln Leu Cys Gln Glu Met His
        580                 585                 590

Asp Leu Tyr Val Ser Phe Asp Val Lys Asp Leu Gln Lys Ala Met Phe
        595                 600                 605

Arg Gln Gln Ser Phe Pro Ser Val Val Met Asn Pro Gln Asp Ala His
        610                 615                 620

Ser Ala Tyr Ile Arg Gly Asp Val Glu Leu Val Arg Ile Arg Asp Ala
625                 630                 635                 640

Glu Gly Arg Ile Ala Ala Glu Gly Ala Leu Pro Tyr Pro Pro Gly Val
            645                 650                 655

Leu Cys Val Val Pro Gly Glu Val Trp Gly Gly Ala Val Gln Arg Tyr

Phe Leu Ala Leu Glu Glu Gly Val Asn Leu Leu Pro Gly Phe Ser Pro
        675                 680                 685

Glu Leu Gln Gly Val Tyr Ser Glu Thr Asp Ala Asp Gly Val Lys Arg
        690                 695                 700

Leu Tyr Gly Tyr Val Leu Lys
705                 710

<210> SEQ ID NO 22
<211> LENGTH: 1536
<212> TYPE: DNA
<213> ORGANISM: Alcaligenes faecalis subsp. faecalis NCIB 8687

<400> SEQUENCE: 22

```
atgctgcaca gtccgactca ccgtcacctc tcacccgttc ccttgtcccc cggccgtcgc      60
tggctgattc tggccattgt atcggcggca ctcttgttga ttgtggtgga catgacggtg     120
ctctacaccg cccttccccg gctgacccat gacctgcagg cgtcggcctc cgacaagctc     180
tggatcatta acagttacgc gctggtcgtc tctggcctgc tgcttggcat gggcacgctg     240
ggagatcgtc tcggccataa cgcctgtttt ctgtctggtc tggccatgtt ggagtggcc      300
tcggtagcag cggcctattc ccccaacccg gcctttctga tcgcggcacg gcatttctg      360
ggcgtggctg ccgccatgat gatgcccgcc acgttgtcat tgattcgcat cactttcac      420
gatgagcgtg aacgcgcagt ggcctttggt gtgtggtcct ccatcgcctc gggcggcgcg     480
gcctttggac cggtcctggg gggctttctg ctggagcact tctggtgggg ctcggtcttt     540
ctgatcaacg tccctatcgt actgatcgcc ctgcccatgg gctggctgct ggtgccgcgt     600
tccacgccgg acagttcccg accctgggat atcaaaggtt ccgtgctgat tatggtgggg     660
ctggttgcca gtaccttggc gatcaaggaa atgggcaagc tctataccga ttggggactg     720
acagcgggag ccctggtggt cggcgtcctc tttctgggct ggtttgtccg gcagcaaaat     780
cgcagtccct ttcctttgct ggattttgcc ctgttcaaaa atgccacgct cagtacggct     840
gttctgtccg ccctgagcgc ttcggccgcc ctgattggca tggagctcgt ttttagccaa     900
cgcctccaac tggtactggg cttctcgccg ctgcaggcgg gtctggccat tattcccttg     960
ccattggccg cattcctggc cggtcccctg gcaggtcgtt tgctgatggt tattggcagc    1020
aagcgtctgc tgatcggctc cctaagcctg gcagcggcag gcatggcggc ttacctgctc    1080
tggcacaaca gtgcccagtt tttgcaggta atcagcctgg tcatgctggg tctgggtata    1140
ggcgcggcca tgactgccgc ctccagcacc atcatgcaaa gtgtgccccc ctcacgtgcc    1200
gggatggtgg cctctgtcga agaaatgtcg tatgaactgg gcggcgcctt gggcgtgacc    1260
ctcatgggct gcctgctgtc gttcgtttat agcgccagcc tgatcttgcc cgagacattg    1320
agcgctcatc ccctggccta cgacagcctg gatcaggccc tgttgataac ggagaacctg    1380
ccacaagagc aggccttcgg attggcgag ttggctcgcg atgccttcga ccgaggctat    1440
gtcgccgtgc tggccagttg tactgtgctg ctggcaatgg ctgcgctggc ggtctggtac    1500
tttcagcgct cccccgggcg ttcgcacgcc gattag                             1536
```

<210> SEQ ID NO 23
<211> LENGTH: 511
<212> TYPE: PRT
<213> ORGANISM: Alcaligenes faecalis subsp. faecalis NCIB 8687

<400> SEQUENCE: 23

```
Met Leu His Ser Pro Thr His Arg His Leu Ser Pro Val Pro Leu Ser
1               5                   10                  15

Pro Gly Arg Arg Trp Leu Ile Leu Ala Ile Val Ser Ala Ala Leu Leu
                20                  25                  30

Leu Ile Val Val Asp Met Thr Val Leu Tyr Thr Ala Leu Pro Arg Leu
            35                  40                  45

Thr His Asp Leu Gln Ala Ser Ala Ser Asp Lys Leu Trp Ile Ile Asn
        50                  55                  60

Ser Tyr Ala Leu Val Val Ser Gly Leu Leu Leu Gly Met Gly Thr Leu
65                  70                  75                  80

Gly Asp Arg Leu Gly His Lys Arg Leu Phe Leu Ser Gly Leu Ala Met
                85                  90                  95

Phe Gly Val Ala Ser Val Ala Ala Ala Tyr Ser Pro Asn Pro Ala Phe
                100                 105                 110

Leu Ile Ala Ala Arg Ala Phe Leu Gly Val Ala Ala Ala Met Met Met
            115                 120                 125

Pro Ala Thr Leu Ser Leu Ile Arg Ile Thr Phe His Asp Glu Arg Glu
        130                 135                 140

Arg Ala Val Ala Phe Gly Val Trp Ser Ser Ile Ala Ser Gly Gly Ala
145                 150                 155                 160

Ala Phe Gly Pro Val Leu Gly Gly Phe Leu Leu Glu His Phe Trp Trp
                165                 170                 175

Gly Ser Val Phe Leu Ile Asn Val Pro Ile Val Leu Ile Ala Leu Pro
                180                 185                 190

Met Gly Trp Leu Leu Val Pro Arg Ser Thr Pro Asp Ser Ser Arg Pro
            195                 200                 205

Trp Asp Ile Lys Gly Ser Val Leu Ile Met Val Gly Leu Val Ala Ser
        210                 215                 220

Thr Leu Ala Ile Lys Glu Met Gly Lys Leu Tyr Thr Asp Trp Gly Leu
225                 230                 235                 240

Thr Ala Gly Ala Leu Val Val Gly Val Leu Phe Leu Gly Trp Phe Val
                245                 250                 255

Arg Gln Gln Asn Arg Ser Pro Phe Pro Leu Leu Asp Phe Ala Leu Phe
                260                 265                 270

Lys Asn Ala Thr Leu Ser Thr Ala Val Leu Ser Ala Leu Ser Ala Ser
            275                 280                 285

Ala Ala Leu Ile Gly Met Glu Leu Val Phe Ser Gln Arg Leu Gln Leu
        290                 295                 300

Val Leu Gly Phe Ser Pro Leu Gln Ala Gly Leu Ala Ile Ile Pro Leu
305                 310                 315                 320

Pro Leu Ala Ala Phe Leu Ala Gly Pro Leu Ala Gly Arg Leu Leu Met
                325                 330                 335

Val Ile Gly Ser Lys Arg Leu Leu Ile Gly Ser Leu Ser Leu Ala Ala
                340                 345                 350

Ala Gly Met Ala Ala Tyr Leu Leu Trp His Asn Ser Ala Gln Phe Leu
            355                 360                 365

Gln Val Ile Ser Leu Val Met Leu Gly Leu Gly Ile Gly Ala Ala Met
        370                 375                 380

Thr Ala Ala Ser Ser Thr Ile Met Gln Ser Val Pro Pro Ser Arg Ala
385                 390                 395                 400

Gly Met Val Ala Ser Val Glu Glu Met Ser Tyr Glu Leu Gly Gly Ala
                405                 410                 415

Leu Gly Val Thr Leu Met Gly Cys Leu Leu Ser Phe Val Tyr Ser Ala
```

```
                420              425              430
Ser Ile Leu Pro Glu Thr Leu Ser Ala His Pro Leu Ala Tyr Asp
            435              440              445

Ser Leu Asp Gln Ala Leu Leu Ile Thr Glu Asn Leu Pro Gln Glu Gln
        450                  455              460

Ala Phe Gly Leu Ala Glu Leu Ala Arg Asp Ala Phe Asp Arg Gly Tyr
465                 470                 475                 480

Val Ala Val Leu Ala Ser Cys Thr Val Leu Leu Ala Met Ala Ala Leu
                485                 490                 495

Ala Val Trp Tyr Phe Gln Arg Ser Pro Gly Arg Ser His Ala Asp
            500                  505              510

<210> SEQ ID NO 24
<211> LENGTH: 1536
<212> TYPE: DNA
<213> ORGANISM: Artificial Sequence
<220> FEATURE:
<223> OTHER INFORMATION: QWA_00075 (Codon optimized sequence)

<400> SEQUENCE: 24
atgttgcact ccccccaccca ccgccacctg tctcctgtgc cgctgtcacc aggtcggcga      60
tggctcatcc tggcaatcgt gtcagcagca cttctgctga tcgtcgtgga tatgacggtt     120
ctgtacactg ctctgccacg ccttacgcat gacctgcagg catccgcttc cgacaaactg     180
tggatcatta actcctatgc acttgtggta tccggtctgc tgctgggtat gggcaccctg     240
ggcgaccgcc tgggccataa cgcctgttc ctgtcaggac ttgcaatgtt cggggttgca     300
tcggttgcag cagcgtactc tccaaatcca gcatttctga tcgcagcacg cgcgtttctg     360
ggtgtggctg cagcaatgat gatgccagca accctctcct tgatccgcat cacctttcac     420
gatgagcgcg aaagggcagt tgcattcggc gtgtggtcct ccatcgcaag tggtggcgca     480
gcattcggtc cagtcctcgg tggcttcctg cttgaacact tctggtgggg ctctgtgttt     540
ctgatcaacg tcccaatcgt gttgatcgca ctcccaatgg gctggctttt agttccacgc     600
agtactccag actcctcccg tccttgggat attaaaggaa gtgttttgat catggttggt     660
ctggtggctt ccaccctggc aatcaaggaa atgggaaagt tgtacaccga ttggggtta     720
accgcaggcg cactggttgt gggtgtgctg ttcctgggat ggttcgtgcg tcaacagaac     780
cgtagcccat ccctcttct ggatttcgcg ctgttcaaga acgcaacact gtctactgca     840
gtgctatccg cactgtccgc atccgctgca ctgattggta tggaactggt gttttcccag     900
cgccttcagc tagtactggg cttcagcccc ctgcaagcag gctggcaat catcccactg     960
ccctggcag catttttggc aggcccactg gcaggccgcc tgctgatggt gatcggctct    1020
aagcgcttac tgattggttc tctgtcactg gcagccgcag gtatggccgc atatctgctg    1080
tggcacaatt ccgcgcagtt ctccaggtg atttccctgg taatgctggg cctgggcatt    1140
ggagctgcaa tgaccgcagc atcttccacc attatgcagt ccgttcctcc atcacgcgca    1200
ggcatggtgg catcggttga ggagatgtcc tacgaattag gaggcgcatt aggagtgaca    1260
ctgatgggct gcctgctgag ctttgtatac tccgcaagcc ttattctgcc agagaccccta    1320
tcagcacacc cactggcata tgactccctg gatcaagcac tgctgatcac tgaaaacctg    1380
ccacaagaac aagcatttgg actggcagag ctagcacgcg acgcattcga tcgaggttac    1440
gtggcagtgc ttcatcttg taccgtgctt cttgcaatgg cagctcttgc agtgtggtac    1500
ttccagcgct cccccaggccg ctcccatgct gattaa                           1536
```

<210> SEQ ID NO 25
<211> LENGTH: 1533
<212> TYPE: DNA
<213> ORGANISM: Stenotrophomonas maltophilia D457

<400> SEQUENCE: 25

| | |
|---|---:|
| atggctttgt cccagccctt ggccggtgct ccggccctgt cgcgtgcccg tcgctgggca | 60 |
| ctgttgttca ccgtcgccgc cggcctgctg ctggtcacgc tcgacaactc cgtgctctac | 120 |
| accgccctgc ccacgctgac cgaagaactc tcggccagtg ccggccaggc gctgtggatc | 180 |
| atcaacgcct atccgctggt gatggccggc ctgctgctgg gcgcgggtac gctgggcgac | 240 |
| cgcatcggcc accgccgcat gttcctgatc ggcctggtgg tgttcggcgt ggcatcgttg | 300 |
| gcagcggcgt cgccgacac cgcagggctg ctgattgccg cgcgcgcctt gctggcggtc | 360 |
| ggcgcggccg cgatgatgcc ggccacgctg gcgctgatcg gcctgagctt ccacgaagcg | 420 |
| cgcgaacgca acatcgccat cgcgatctgg ggttcggtgg ccatcgtcgg cgcggcactc | 480 |
| ggcccgatca tcggtggctg gctgctgcag catttctggt ggggctcggt gttcctgatc | 540 |
| aacgtgccgg tggtggtggt cgcgttcgtg gccacgctgc tgctggcacc ggaaggccag | 600 |
| cgcgacacct cgcgaccgtg ggacctgatt tcgtcgctgc tggctctggc tgcactgtcc | 660 |
| ggcctggtgc tggcgatcaa gtcgctgatc gctacgccgc cgtcgtatgc gctgggtgca | 720 |
| ggcgcgctgc tgctggccgc catcagtggt gcggcgttcg cgcgccgcca gcagcagctg | 780 |
| ccgcacccgc tgctggactt cgcgatcttc cgcaatccgg cgttcctggc cggcacgctg | 840 |
| tcggcggtgt tcaccctgtt tgcgatggcc ggcctgcagc tggtcactac ccagcgcttc | 900 |
| cagctggtgg cgggcttttc tccgctgcag gcgggcctgc tggtgtcggt ggccgcgctg | 960 |
| ggcagcctgc ccagtgcgct gctgggcggc agcatcctgc accgggtggg cctgcgcccg | 1020 |
| ctgatctgtg gcggcctggc cgcaggtgcg ctgggtgtcg gcgtggtggc attcggcttc | 1080 |
| ccgcacggcc tcgctgggt ggtcgccggc atggcgatca ccggcttcgg catgggttcg | 1140 |
| gccatctcgg tggcgtccac cgccatcctc aacaacgtac cggcgcaccg tgcgggcatg | 1200 |
| gcctcgtcgg tggaagaggt gtcctacgag ttcggcggcc tgctggcggt ggcgatgctg | 1260 |
| ggcagcttga gcgcggcgat gtatggcgca ttcctgccgg tctcggccga catgcccgcg | 1320 |
| cttgcacggg aaggcttcac ccaggcgctg cacgtgcac gtgaaagcgg gcagggcgag | 1380 |
| tggttcgcac tggccacgac cgcgtatgac cgcggctacc agatcgtgct gctggtgatc | 1440 |
| acggtggtgc tggcgctggg cgcgtcgatc atcgcgcgcc tgctgcgcgg gcgcgtcggc | 1500 |
| agccgcgagg gtgcggccga tcgcgtaaaa tga | 1533 |

<210> SEQ ID NO 26
<211> LENGTH: 510
<212> TYPE: PRT
<213> ORGANISM: Stenotrophomonas maltophilia D457

<400> SEQUENCE: 26

Met Ala Leu Ser Gln Pro Leu Ala Gly Ala Pro Ala Leu Ser Arg Ala
1               5                   10                  15

Arg Arg Trp Ala Leu Leu Phe Thr Val Ala Ala Gly Leu Leu Leu Val
            20                  25                  30

Thr Leu Asp Asn Ser Val Leu Tyr Thr Ala Leu Pro Thr Leu Thr Glu
        35                  40                  45

Glu Leu Ser Ala Ser Ala Gly Gln Ala Leu Trp Ile Ile Asn Ala Tyr
    50                  55                  60

-continued

```
Pro Leu Val Met Ala Gly Leu Leu Gly Ala Gly Thr Leu Gly Asp
 65                  70                  75                  80

Arg Ile Gly His Arg Arg Met Phe Leu Ile Gly Leu Val Val Phe Gly
                 85                  90                  95

Val Ala Ser Leu Ala Ala Ala Phe Ala Asp Thr Ala Gly Leu Leu Ile
                100                 105                 110

Ala Ala Arg Ala Leu Leu Ala Val Gly Ala Ala Met Met Pro Ala
                115                 120                 125

Thr Leu Ala Leu Ile Gly Leu Ser Phe His Glu Ala Arg Glu Arg Asn
130                 135                 140

Ile Ala Ile Ala Ile Trp Gly Ser Val Ala Ile Val Gly Ala Ala Leu
145                 150                 155                 160

Gly Pro Ile Ile Gly Gly Trp Leu Leu Gln His Phe Trp Trp Gly Ser
                165                 170                 175

Val Phe Leu Ile Asn Val Pro Val Val Val Ala Phe Val Ala Thr
                180                 185                 190

Leu Leu Leu Ala Pro Glu Gly Gln Arg Asp Thr Ser Arg Pro Trp Asp
                195                 200                 205

Leu Ile Ser Ser Leu Leu Ala Leu Ala Ala Leu Ser Gly Leu Val Leu
210                 215                 220

Ala Ile Lys Ser Leu Ile Ala Thr Pro Pro Ser Tyr Ala Leu Gly Ala
225                 230                 235                 240

Gly Ala Leu Leu Leu Ala Ala Ile Ser Gly Ala Ala Phe Ala Arg Arg
                245                 250                 255

Gln Gln Gln Leu Pro His Pro Leu Leu Asp Phe Ala Ile Phe Arg Asn
                260                 265                 270

Pro Ala Phe Leu Ala Gly Thr Leu Ser Ala Val Phe Thr Leu Phe Ala
                275                 280                 285

Met Ala Gly Leu Gln Leu Val Thr Thr Gln Arg Phe Gln Leu Val Ala
                290                 295                 300

Gly Phe Ser Pro Leu Gln Ala Gly Leu Leu Val Ser Val Ala Ala Leu
305                 310                 315                 320

Gly Ser Leu Pro Ser Ala Leu Leu Gly Gly Ser Ile Leu His Arg Val
                325                 330                 335

Gly Leu Arg Pro Leu Ile Cys Gly Gly Leu Ala Ala Gly Ala Leu Gly
                340                 345                 350

Val Gly Val Val Ala Phe Gly Phe Pro His Gly Leu Gly Trp Val Val
                355                 360                 365

Ala Gly Met Ala Ile Thr Gly Phe Gly Met Gly Ser Ala Ile Ser Val
                370                 375                 380

Ala Ser Thr Ala Ile Leu Asn Asn Val Pro Ala His Arg Ala Gly Met
385                 390                 395                 400

Ala Ser Ser Val Glu Glu Val Ser Tyr Glu Phe Gly Gly Leu Leu Ala
                405                 410                 415

Val Ala Met Leu Gly Ser Leu Ser Ala Ala Met Tyr Gly Ala Phe Leu
                420                 425                 430

Pro Val Ser Ala Asp Met Pro Ala Leu Ala Arg Glu Gly Phe Thr Gln
                435                 440                 445

Ala Leu His Val Ala Arg Glu Ser Gly Gln Gly Glu Trp Phe Ala Leu
                450                 455                 460

Ala Thr Thr Ala Tyr Asp Arg Gly Tyr Gln Ile Val Leu Leu Val Ile
465                 470                 475                 480
```

Thr Val Val Leu Ala Leu Gly Ala Ser Ile Ile Ala Arg Leu Leu Arg
            485                 490                 495

Gly Arg Val Gly Ser Arg Glu Gly Ala Ala Asp Arg Val Lys
        500                 505                 510

<210> SEQ ID NO 27
<211> LENGTH: 1512
<212> TYPE: DNA
<213> ORGANISM: Artificial Sequence
<220> FEATURE:
<223> OTHER INFORMATION: SMD_2351 (Codon optimized sequence)

<400> SEQUENCE: 27

| | | |
|---|---|---|
| atgccagcag cgcattcaaa tagatgggta ctgctggtga ccgtggcagc aggcctcctg | 60 |
| ctgatcgtcc tggataattc cgttctatac accgcactgc aaccctgac acggaactg | 120 |
| ggcgcaacgg caacccaggg tctgtggatc atcaacgcat atccactggt gatggcaggc | 180 |
| cttttactgg gtaccggtac tttgggcgat cgcatcggcc accgccgat gtttctgata | 240 |
| ggactggtgc ttttcggcgt agcaagtatc gtcgcagcat actcccctac tgcagaaatc | 300 |
| ttaatcggtg cacgtgcatt tctggccgtg ggcgcagcag caatgatgcc cgcaaccctt | 360 |
| gcactgatcc gtgtgacctt cgaggacgac cgcgaacgca acattgcaat gcaatctgg | 420 |
| ggctcattgt cagtagtggg agcagcactg ggcccaatta ttggcggctt tctgctgggc | 480 |
| catttctggt ggggctccgt gttcctgatc aacgttccag ttgtggtggc agcattcatc | 540 |
| tccgcattga ttgtggcacc gaaagtcgct ggcgacgcaa ctaagccatg ggatgttgta | 600 |
| tcctcatttc aagcactggt tgcgttgagt gcattcgtca tcgcaattaa ggaatctgct | 660 |
| catgcaggcc agtcctgggc agttccggca atctctttgc tggtcgcaat tctggcaggg | 720 |
| gcactgttcg tgcgccgtca gttgcgcctg ccttcccac tgttagattt ctccatttc | 780 |
| cgcaatgcag cttttacttc cggagttctg gcagcagctt tttctttgtt cgctatcgt | 840 |
| ggagtggaac tagctacaac ccaacgcttc caactggtgg caggcttcac tccactggag | 900 |
| gcaggcatgc ttgtgtccgc agcagcgctt ggctctctgc ctaccgcatt gttgggaggt | 960 |
| gcattcctgc accgaattgg actgcgaatc cttatcgcag gcggcctggc tgcaggctcg | 1020 |
| cttgctgtcc ttctggcaac ctggggcatt acgcacggcc tgggctggct gatcgcaggc | 1080 |
| cttgcactga ccggcgcagg cgtgggtgca accatgtccg tggcatccac cgcaatcgtt | 1140 |
| ggcaacgtgc cggttcaccg tgcaggaatg gcatcctccg ttgaagaggt ttcctacgag | 1200 |
| ttcggttcct tgtttgcagt gacgatttta gggtccctac tggcatacct atacacagtg | 1260 |
| aacgtggttt ttccagcagg cacctctgaa gcagcaaggg attccatggc aagcgcattg | 1320 |
| gtgttcgcaa acgaagcagg agcagacgga gtggtagttc gccaggccgc aggaatcgca | 1380 |
| tttgatcacg catataccgt tgtgatgtac gtcgcagcag gcgtactggc agtgggcgca | 1440 |
| ctgattaccg gtatcctcct gcgccgttac ggtccaggct cccaatcctc tgcctatcca | 1500 |
| actcagcact aa | 1512 |

<210> SEQ ID NO 28
<211> LENGTH: 36
<212> TYPE: DNA
<213> ORGANISM: Artificial Sequence
<220> FEATURE:
<223> OTHER INFORMATION: QWA_00075-F Primer

<400> SEQUENCE: 28
caacgaaagg aaacactatg ttgcactccc ccaccc          36

<210> SEQ ID NO 29
<211> LENGTH: 37
<212> TYPE: DNA
<213> ORGANISM: Artificial Sequence
<220> FEATURE:
<223> OTHER INFORMATION: QWA_00075-R Primer

<400> SEQUENCE: 29
gaatgagttc ctcgagttaa tcagcatggg agcggcc        37

<210> SEQ ID NO 30
<211> LENGTH: 40
<212> TYPE: DNA
<213> ORGANISM: Artificial Sequence
<220> FEATURE:
<223> OTHER INFORMATION: SMD_2351-F Primer

<400> SEQUENCE: 30
caacgaaagg aaacactatg ccagcagcgc attcaaatag      40

<210> SEQ ID NO 31
<211> LENGTH: 39
<212> TYPE: DNA
<213> ORGANISM: Artificial Sequence
<220> FEATURE:
<223> OTHER INFORMATION: SMD_2351-R Primer

<400> SEQUENCE: 31
gaatgagttc ctcgagttag tgctgagttg gataggcag       39

<210> SEQ ID NO 32
<211> LENGTH: 2142
<212> TYPE: DNA
<213> ORGANISM: Escherichia coli

<400> SEQUENCE: 32
atgaacatca ttgccattat gggaccgcat ggcgtctttt ataaagatga gcccatcaaa        60
gaactggagt cggcgctggt ggcgcaaggc tttcagatta tctggccaca aaacagcgtt       120
gatttgctga aatttatcga gcataaccct cgaatttgcg gcgtgatttt tgactgggat       180
gagtacagtc tcgatttatg tagcgatatc aatcagctta tgaatatcct cccgctttat       240
gccttcatca cacccactc gacgatggat gtcagcgtgc aggatatgcg gatggcgctc       300
tggttttttg aatatgcgct ggggcaggcg gaagatatcg ccattcgtat gcgtcagtac       360
accgacgaat atcttgataa cattacaccg ccgttcacga aagccttgtt tacctacgtc       420
aaagagcgga agtacacctt ttgtacgccg gggcatatgg gcggcaccgc atatcaaaaa       480
agcccggttg gctgtctgtt ttatgatttt ttcggcggga atactcttaa ggctgatgtc       540
tctatttcgg tcaccgagct tggttcgttg ctcgaccaca ccgggccaca cctggaagcg       600
gaagagtaca tcgcgcggac ttttggcgcg aacagagtt atatcgttac caacggaaca       660
tcgacgtcga acaaaattgt gggtatgtac gccgcgccat ccggcagtac gctgttgatc       720
gaccgcaatt gtcataaatc gctggcgcat ctgttgatga tgaacgatgt agtgccagtc       780
tggctgaaac cgacgcgtaa tgcgttgggg attcttggtg ggatcccgcg ccgtgaattt       840
actcgcgaca gcatcgaaga gaaagtcgct gctaccacgc aagcacaatg gccggttcat       900
gcggtgatca ccaactccac ctatgatggc ttgctctaca acaccgactg gatcaaacag       960
acgctggatg tcccgtcgat tcacttcgat tctgcctggg tgccgtacac ccatttttcat      1020

```
ccgatctacc agggtaaaag tggtatgagc ggcgagcgtg ttgcgggaaa agtgatcttc    1080
gaaacgcaat cgacccacaa aatgctggcg gcgttatcgc aggcttcgct gatccacatt    1140
aaaggcgagt atgacgaaga ggcctttaac gaagccttta tgatgcatac caccacctcg    1200
cccagttatc ccattgttgc ttcggttgag acggcggcgg cgatgctgcg tggtaatccg    1260
ggcaaacggc tgattaaccg ttcagtagaa cgagctctgc attttcgcaa agaggtccag    1320
cggctgcggg aagagtctga cggttggttt ttcgatatct ggcaaccgcc gcaggtggat    1380
gaagccgaat gctggcccgt tgcgcctggc gaacagtggc acggctttaa cgatgcggat    1440
gccgatcata tgtttctcga tccggttaaa gtcactattt tgacaccggg gatggacgag    1500
cagggcaata tgagcgagga ggggatcccg gcggcgctgg tagcaaaatt cctcgacgaa    1560
cgtgggatcg tagtagagaa aaccggcccc tataacctgc tgtttctctt tagtattggc    1620
atcgataaaa ccaaagcaat gggattattg cgtgggttga cggaattcaa acgctcttac    1680
gatctcaacc tgcggatcaa aaatatgcta cccgatctct atgcagaaga tcccgatttc    1740
taccgcaata tgcgtattca ggatctggca caagggatcc ataagctgat tcgtaaacac    1800
gatcttcccg gtttgatgtt gcgggcattc gatactttgc cggagatgat catgacgcca    1860
catcaggcat ggcaacgaca aattaaaggc gaagtagaaa ccattgcgct ggaacaactg    1920
gtcggtagag tatcggcaaa tatgatcctg ccttatccac cgggcgtacc gctgttgatg    1980
cctggagaaa tgctgaccaa agagagccga acagtactcg atttctctact gatgctttgt    2040 tccgtcgggc aacattaccc cggttttgaa acggatattc acggcgcgaa acaggacgaa    2100
gacggcgttt accgcgtacg agtcctaaaa atggcgggat aa                      2142
```

<210> SEQ ID NO 33
<211> LENGTH: 713
<212> TYPE: PRT
<213> ORGANISM: Escherichia coli

<400> SEQUENCE: 33

```
Met Asn Ile Ile Ala Ile Met Gly Pro His Gly Val Phe Tyr Lys Asp
1               5                   10                  15

Glu Pro Ile Lys Glu Leu Glu Ser Ala Leu Val Ala Gln Gly Phe Gln
            20                  25                  30

Ile Ile Trp Pro Gln Asn Ser Val Asp Leu Leu Lys Phe Ile Glu His
        35                  40                  45

Asn Pro Arg Ile Cys Gly Val Ile Phe Asp Trp Asp Glu Tyr Ser Leu
    50                  55                  60

Asp Leu Cys Ser Asp Ile Asn Gln Leu Asn Glu Tyr Leu Pro Leu Tyr
65                  70                  75                  80

Ala Phe Ile Asn Thr His Ser Thr Met Asp Val Ser Val Gln Asp Met
                85                  90                  95

Arg Met Ala Leu Trp Phe Phe Glu Tyr Ala Leu Gly Gln Ala Glu Asp
            100                 105                 110

Ile Ala Ile Arg Met Arg Gln Tyr Thr Asp Glu Tyr Leu Asp Asn Ile
        115                 120                 125

Thr Pro Pro Phe Thr Lys Ala Leu Phe Thr Tyr Val Lys Glu Arg Lys
    130                 135                 140

Tyr Thr Phe Cys Thr Pro Gly His Met Gly Gly Thr Ala Tyr Gln Lys
145                 150                 155                 160

Ser Pro Val Gly Cys Leu Phe Tyr Asp Phe Phe Gly Gly Asn Thr Leu
                165                 170                 175
```

```
Lys Ala Asp Val Ser Ile Ser Val Thr Glu Leu Gly Ser Leu Leu Asp
            180                 185                 190
His Thr Gly Pro His Leu Glu Ala Glu Tyr Ile Ala Arg Thr Phe
        195                 200                 205
Gly Ala Glu Gln Ser Tyr Ile Val Thr Asn Gly Thr Ser Thr Ser Asn
        210                 215                 220
Lys Ile Val Gly Met Tyr Ala Ala Pro Ser Gly Ser Thr Leu Leu Ile
225                 230                 235                 240
Asp Arg Asn Cys His Lys Ser Leu Ala His Leu Leu Met Met Asn Asp
                245                 250                 255
Val Val Pro Val Trp Leu Lys Pro Thr Arg Asn Ala Leu Gly Ile Leu
            260                 265                 270
Gly Gly Ile Pro Arg Arg Glu Phe Thr Arg Asp Ser Ile Glu Glu Lys
        275                 280                 285
Val Ala Ala Thr Thr Gln Ala Gln Trp Pro Val His Ala Val Ile Thr
        290                 295                 300
Asn Ser Thr Tyr Asp Gly Leu Leu Tyr Asn Thr Asp Trp Ile Lys Gln
305                 310                 315                 320
Thr Leu Asp Val Pro Ser Ile His Phe Asp Ser Ala Trp Val Pro Tyr
                325                 330                 335
Thr His Phe His Pro Ile Tyr Gln Gly Lys Ser Gly Met Ser Gly Glu
            340                 345                 350
Arg Val Ala Gly Lys Val Ile Phe Glu Thr Gln Ser Thr His Lys Met
        355                 360                 365
Leu Ala Ala Leu Ser Gln Ala Ser Leu Ile His Ile Lys Gly Glu Tyr
        370                 375                 380
Asp Glu Glu Ala Phe Asn Glu Ala Phe Met Met His Thr Thr Thr Ser
385                 390                 395                 400
Pro Ser Tyr Pro Ile Val Ala Ser Val Glu Thr Ala Ala Ala Met Leu
                405                 410                 415
Arg Gly Asn Pro Gly Lys Arg Leu Ile Asn Arg Ser Val Glu Arg Ala
            420                 425                 430
Leu His Phe Arg Lys Glu Val Gln Arg Leu Arg Glu Glu Ser Asp Gly
        435                 440                 445
Trp Phe Phe Asp Ile Trp Gln Pro Pro Gln Val Asp Glu Ala Glu Cys
        450                 455                 460
Trp Pro Val Ala Pro Gly Glu Gln Trp His Gly Phe Asn Asp Ala Asp
465                 470                 475                 480
Ala Asp His Met Phe Leu Asp Pro Val Lys Val Thr Ile Leu Thr Pro
                485                 490                 495
Gly Met Asp Glu Gln Gly Asn Met Ser Glu Glu Gly Ile Pro Ala Ala
            500                 505                 510
Leu Val Ala Lys Phe Leu Asp Glu Arg Gly Ile Val Val Glu Lys Thr
        515                 520                 525
Gly Pro Tyr Asn Leu Leu Phe Leu Phe Ser Ile Gly Ile Asp Lys Thr
        530                 535                 540
Lys Ala Met Gly Leu Leu Arg Gly Leu Thr Glu Phe Lys Arg Ser Tyr
545                 550                 555                 560
Asp Leu Asn Leu Arg Ile Lys Asn Met Leu Pro Asp Leu Tyr Ala Glu
                565                 570                 575
Asp Pro Asp Phe Tyr Arg Asn Met Arg Ile Gln Asp Leu Ala Gln Gly
            580                 585                 590
Ile His Lys Leu Ile Arg Lys His Asp Leu Pro Gly Leu Met Leu Arg
```

```
              595                 600                 605
Ala Phe Asp Thr Leu Pro Glu Met Ile Met Thr Pro His Gln Ala Trp
    610                 615                 620

Gln Arg Gln Ile Lys Gly Glu Val Glu Thr Ile Ala Leu Glu Gln Leu
625                 630                 635                 640

Val Gly Arg Val Ser Ala Asn Met Ile Leu Pro Tyr Pro Pro Gly Val
                645                 650                 655

Pro Leu Leu Met Pro Gly Glu Met Leu Thr Lys Glu Ser Arg Thr Val
            660                 665                 670

Leu Asp Phe Leu Leu Met Leu Cys Ser Val Gly Gln His Tyr Pro Gly
        675                 680                 685

Phe Glu Thr Asp Ile His Gly Ala Lys Gln Asp Glu Asp Gly Val Tyr
    690                 695                 700

Arg Val Arg Val Leu Lys Met Ala Gly
705                 710

<210> SEQ ID NO 34
<211> LENGTH: 33
<212> TYPE: DNA
<213> ORGANISM: Artificial Sequence
<220> FEATURE:
<223> OTHER INFORMATION: CJ7-F_KpnI Primer

<400> SEQUENCE: 34 cgggtacca gaaacatccc agcgctacta ata                                33

<210> SEQ ID NO 35
<211> LENGTH: 32
<212> TYPE: DNA
<213> ORGANISM: Artificial Sequence
<220> FEATURE:
<223> OTHER INFORMATION: CJ7-R-HindIII Primer

<400> SEQUENCE: 35
cccaagctta gtgtttcctt tcgttgggta cg                                32

<210> SEQ ID NO 36
<211> LENGTH: 38
<212> TYPE: DNA
<213> ORGANISM: Artificial Sequence
<220> FEATURE:
<223> OTHER INFORMATION: ldcC-F_HindIII Primer

<400> SEQUENCE: 36
cccaagctta agcttatgaa catcattgcc attatggg                          38

<210> SEQ ID NO 37
<211> LENGTH: 32
<212> TYPE: DNA
<213> ORGANISM: Artificial Sequence
<220> FEATURE:
<223> OTHER INFORMATION: ldcC-R_XbaI Primer

<400> SEQUENCE: 37
tgctctagat tatcccgcca tttttaggac tc                                32
```